United States Patent
Patra et al.

(10) Patent No.: US 11,033,642 B2
(45) Date of Patent: Jun. 15, 2021

(54) MULTIDENTATE BIFUNCTIONAL CHELATING AGENTS FOR RADIONUCLIDE COMPLEXATION IN DIAGNOSTICS AND THERAPY

(71) Applicants: UNIVERSITAT ZURICH, Zurich (CH); UNIVERSITATSSPITAL BASEL, Basel (CH)

(72) Inventors: Malay Patra, Cambridge, MA (US); Gilles Gasser, Zug (CH); Thomas L. Mindt, Basel (CH); Andreas Bauman, Schopfheim (DE)

(73) Assignees: UNIVERSITAT ZURICH, Zurich (CH); UNIVERSITATSSPITAL BASEL, Basel (CH)

( * ) Notice: Subject to any disclaimer, the term of this patent is extended or adjusted under 35 U.S.C. 154(b) by 270 days.

(21) Appl. No.: 15/127,025

(22) PCT Filed: Mar. 18, 2015

(86) PCT No.: PCT/EP2015/055684
§ 371 (c)(1),
(2) Date: Sep. 18, 2016

(87) PCT Pub. No.: WO2015/140212
PCT Pub. Date: Sep. 24, 2015

(65) Prior Publication Data
US 2017/0106106 A1    Apr. 20, 2017

(30) Foreign Application Priority Data
Mar. 19, 2014    (EP) .................................... 14160792

(51) Int. Cl.
| | | |
|---|---|---|
| *A61K 51/08* | (2006.01) | |
| *C07F 7/00* | (2006.01) | |
| *A61K 51/04* | (2006.01) | |
| *C07K 7/08* | (2006.01) | |
| *C08G 69/10* | (2006.01) | |
| *C08G 69/08* | (2006.01) | |
| *C08G 69/48* | (2006.01) | |
| *C08G 69/26* | (2006.01) | |
| *C07C 235/74* | (2006.01) | |

(52) U.S. Cl.
CPC ........ *A61K 51/088* (2013.01); *A61K 51/0478* (2013.01); *C07C 235/74* (2013.01); *C07F 7/003* (2013.01); *C07K 7/08* (2013.01); *C08G 69/08* (2013.01); *C08G 69/10* (2013.01); *C08G 69/26* (2013.01); *C08G 69/48* (2013.01)

(58) Field of Classification Search
CPC .......... C07K 7/08; C08G 69/08; C08G 69/26; C08G 69/48; C08G 69/10; C07F 7/003; C07C 235/74; A61K 51/0478; A61K 51/088
See application file for complete search history.

(56) References Cited

U.S. PATENT DOCUMENTS

2006/0030619 A1*  2/2006  Liu ...................... A61K 31/195
                                                514/458
2010/0273847 A1* 10/2010  Codd ..................... C07C 259/06
                                                514/387

FOREIGN PATENT DOCUMENTS

| WO | WO 00/04868 A2 | 2/2002 |
| WO | 03006070 | 1/2003 |
| WO | 2013088395 | 6/2013 |
| WO | WO 2014/164988 | 10/2014 |

OTHER PUBLICATIONS

Ng et al., Inorg. Chem., 1989, 28(11), p. 2062-2066 (Year: 1989).*
Malay Patra et al:"An octadentate bifunctional chelating agent for the development of stable zirconium-89 based molecular imaging probes", Chemical Communications < Chemical Communications—ChemCom, vol. 50, No. 78, Jan. 1, 2014, pp. 11523-11525.
Amruta R. Poreddy et al: "Hydroxamate-Based Iron Chelators: Combinatorial Syntheses of Desferrioxamine B Analogues and Evaluation of Binding Affinities", Journal of Combinatorial Chemistry, vol. 6, No. 2, Mar. 1, 2004, pp. 239-254.
Guérard, F., Lee, Y.S. and Brechbiel, M.W., 2014. Rational design, synthesis and evaluation of tetrahydroxamic acid chelators for stable complexation of ZrIV. Chemistry (Weinheim an der Bergstrasse, Germany), 20(19), p. 5584.
Fischer, Gabriel, et al. "89Zr, a radiometal nuclide with high potential for molecular imaging with PET: chemistry, applications and remaining challenges." Molecules 18.6 (2013): 6469-6490.
Brans, Luc, et al. "Synthesis and Evaluation of Bombesin Analogues Conjugated to Two Different Triazolyl-Derived Chelators for 99mTc Labeling." ChemMedChem 5.10 (2010): 1717-1725.
Zhang, Chunfu, et al. "Specific targeting of tumor angiogenesis by RGD-conjugated ultrasmall superparamagnetic iron oxide particles using a clinical 1.5-T magnetic resonance scanner." Cancer research 67.4 (2007): 1555-1562.

* cited by examiner

*Primary Examiner* — Michael G. Hartley
*Assistant Examiner* — Leah H Schlientz
(74) *Attorney, Agent, or Firm* — JMB Davis Ben-David

(57) ABSTRACT

The invention relates to octadentate ligands of a general formula $R^1$-D-X-D-X-D-X-D-E-$R^2$, wherein D is C(O)N(OH) or N(OH)C(O), pyrimidinone or pyridinone, each X independently of any other X is a saturated or partially unsaturated, substituted or unsubstituted linker comprising 8-11 atoms selected from any of N, C, O; $R^1$ is alkyl, cycloalkyl, arene, or heteroarene, E is a saturated or partially unsaturated, substituted or unsubstituted chain comprising 1-50 atoms and $R^2$ is a moiety capable of selectively binding to a biomolecule, or a nanoparticle. The invention further relates to complexes of the ligand, particularly radionuclides and their use in radioimmunotherapy and imaging.

20 Claims, 2 Drawing Sheets
Specification includes a Sequence Listing.

Complex III

SEQUENCE LISTING

<160> NUMBER OF SEQ ID NOS: 14

<210> SEQ ID NO 1
<211> LENGTH: 14
<212> TYPE: PRT
<213> ORGANISM: Bombina bombina

<400> SEQUENCE: 1

Gln Gln Arg Leu Gly Asn Gln Trp Ala Val Gly His Leu Met
1               5                   10

<210> SEQ ID NO 2
<211> LENGTH: 116
<212> TYPE: PRT
<213> ORGANISM: homo sapiens

<400> SEQUENCE: 2

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
            20                  25                  30

Gln Phe Leu Gln Lys Ser Leu Ala Ala Ala Ala Gly Lys Gln Glu Leu
        35                  40                  45

Ala Lys Tyr Phe Leu Ala Glu Leu Leu Ser Glu Pro Asn Gln Thr Glu
            50                  55                  60

Asn Asp Ala Leu Glu Pro Glu Asp Leu Ser Gln Ala Ala Glu Gln Asp
 65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
            115

<210> SEQ ID NO 3
<211> LENGTH: 101
<212> TYPE: PRT
<213> ORGANISM: homo sapiens

<400> SEQUENCE: 3

Met Gln Arg Leu Cys Val Tyr Val Leu Ile Phe Ala Leu Ala Leu Ala
 1               5                  10                  15

Ala Phe Ser Glu Ala Ser Trp Lys Pro Arg Ser Gln Gln Pro Asp Ala
                20                  25                  30

Pro Leu Gly Thr Gly Ala Asn Arg Asp Leu Glu Leu Pro Trp Leu Glu
            35                  40                  45

Gln Gln Gly Pro Ala Ser His His Arg Arg Gln Leu Gly Pro Gln Gly
         50                  55                  60

Pro Pro His Leu Val Ala Asp Pro Ser Lys Lys Gln Gly Pro Trp Leu
 65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 4
<211> LENGTH: 11
<212> TYPE: PRT
<213> ORGANISM: HIV

<400> SEQUENCE: 4

Tyr Gly Arg Lys Lys Arg Arg Gln Arg Arg Arg
 1               5                  10

<210> SEQ ID NO 5
<211> LENGTH: 261
<212> TYPE: PRT
<213> ORGANISM: homo sapiens

<400> SEQUENCE: 5

Met Trp Val Pro Val Val Phe Leu Thr Leu Ser Val Thr Trp Ile Gly
 1               5                  10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
         50                  55                  60

His Cys Ile Arg Asn Lys Ser Val Ile Leu Leu Gly Arg His Ser Leu
 65                  70                  75                  80

-continued

```
Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
            130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
            195                 200                 205

Cys Ser Gly Asp Ser Gly Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260
```

<210> SEQ ID NO 6
<211> LENGTH: 97
<212> TYPE: PRT
<213> ORGANISM: homo sapiens

<400> SEQUENCE: 6

```
Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
                20                  25                  30

Pro Asp Asn Pro Gly Glu Asp Ala Pro Ala Glu Asp Met Ala Arg Tyr
            35                  40                  45

Tyr Ser Ala Leu Arg His Tyr Ile Asn Leu Ile Thr Arg Gln Arg Tyr
50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                85                  90                  95

Trp
```

<210> SEQ ID NO 7
<211> LENGTH: 8
<212> TYPE: PRT
<213> ORGANISM: artificial
<220> FEATURE:
<223> OTHER INFORMATION: somatostatin mimic developed by Novartis
      pharmaceuticals

<400> SEQUENCE: 7

```
Phe Cys Phe Trp Lys Tyr Cys Thr
1               5
```

<210> SEQ ID NO 8
<211> LENGTH: 153
<212> TYPE: PRT
<213> ORGANISM: homo sapiens

<400> SEQUENCE: 8

Met Val Ala Thr Lys Thr Phe Ala Leu Leu Leu Ser Leu Phe Leu
1               5                   10                  15

Ala Val Gly Leu Gly Glu Lys Lys Glu Gly His Phe Ser Ala Leu Pro
            20                  25                  30

Ser Leu Pro Val Gly Ser His Ala Lys Val Ser Ser Pro Gln Pro Arg
            35                  40                  45

Gly Pro Arg Tyr Ala Glu Gly Thr Phe Ile Ser Asp Tyr Ser Ile Ala
        50                  55                  60

Met Asp Lys Ile His Gln Gln Asp Phe Val Asn Trp Leu Leu Ala Gln
65                  70                  75                  80

Lys Gly Lys Lys Asn Asp Trp Lys His Asn Ile Thr Gln Arg Glu Ala
                85                  90                  95

Arg Ala Leu Glu Leu Ala Ser Gln Ala Asn Arg Lys Glu Glu Ala
            100                 105                 110

Val Glu Pro Gln Ser Ser Pro Ala Lys Asn Pro Ser Asp Glu Asp Leu
            115                 120                 125

Leu Arg Asp Leu Leu Ile Gln Glu Leu Leu Ala Cys Leu Leu Asp Gln
        130                 135                 140

Thr Asn Leu Cys Arg Leu Arg Ser Arg
145                 150

<210> SEQ ID NO 9
<211> LENGTH: 129
<212> TYPE: PRT
<213> ORGANISM: homo sapiens

<400> SEQUENCE: 9

Met Lys Ile Leu Val Ala Leu Ala Val Phe Phe Leu Val Ser Thr Gln
1               5                   10                  15

Leu Phe Ala Glu Glu Ile Gly Ala Asn Asp Asp Leu Asn Tyr Trp Ser
            20                  25                  30

Asp Trp Tyr Asp Ser Asp Gln Ile Lys Glu Glu Leu Pro Glu Pro Phe
        35                  40                  45

Glu His Leu Leu Gln Arg Ile Ala Arg Arg Pro Lys Pro Gln Gln Phe
    50                  55                  60

Phe Gly Leu Met Gly Lys Arg Asp Ala Asp Ser Ser Ile Glu Lys Gln
65                  70                  75                  80

Val Ala Leu Leu Lys Ala Leu Tyr Gly His Gly Gln Ile Ser His Lys
                85                  90                  95

Arg His Lys Thr Asp Ser Phe Val Gly Leu Met Gly Lys Arg Ala Leu
            100                 105                 110

Asn Ser Val Ala Tyr Glu Arg Ser Ala Met Gln Asn Tyr Glu Arg Arg
            115                 120                 125

Arg

<210> SEQ ID NO 10
<211> LENGTH: 170
<212> TYPE: PRT
<213> ORGANISM: homo sapiens

<400> SEQUENCE: 10

```
Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Met Lys Ala
            20                  25                  30

Leu Glu Ala Asp Phe Leu Thr Asn Met His Thr Ser Lys Ile Ser Lys
        35                  40                  45

Ala His Val Pro Ser Trp Lys Met Thr Leu Leu Asn Val Cys Ser Leu
    50                  55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
                85                  90                  95

Ser Leu Glu Ala Met Leu Thr Ile Tyr Gln Leu His Lys Ile Cys His
            100                 105                 110

Ser Arg Ala Phe Gln His Trp Glu Leu Ile Gln Glu Asp Ile Leu Asp
        115                 120                 125

Thr Gly Asn Asp Lys Asn Gly Lys Glu Glu Val Ile Lys Arg Lys Ile
    130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165                 170

<210> SEQ ID NO 11
<211> LENGTH: 39
<212> TYPE: PRT
<213> ORGANISM: Heloderma suspectum

<400> SEQUENCE: 11

His Gly Gly Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Heloderma suspectum

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 13
<211> LENGTH: 11
<212> TYPE: PRT
<213> ORGANISM: homo sapiens

<400> SEQUENCE: 13

Arg Pro Lys Pro Gln Gln Phe Phe Gly Leu Met
1               5                   10
```

```
<210> SEQ ID NO 14
<211> LENGTH: 11
<212> TYPE: PRT
<213> ORGANISM: Artificial Sequence
<220> FEATURE:
<223> OTHER INFORMATION: modified bombesin peptide
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (3)..(3)
<223> OTHER INFORMATION: bAla
<220> FEATURE:
<221> NAME/KEY: MOD_RES
<222> LOCATION: (11)..(11)
<223> OTHER INFORMATION: AMIDATION, Nle

<400> SEQUENCE: 14

Xaa Xaa Xaa Gln Trp Ala Val Gly His Leu Xaa
1               5                   10
```

MULTIDENTATE BIFUNCTIONAL CHELATING AGENTS FOR RADIONUCLIDE COMPLEXATION IN DIAGNOSTICS AND THERAPY

CROSS-REFERENCE TO RELATED APPLICATIONS

This is the U.S. National Stage of International Application No. PCT/EP2015/055684 filed Mar. 18, 2015, which was published in English under PCT Article 21(2), and which in turn claims the benefit of European Patent Application No. 14160792.9 filed on Mar. 19, 2014.

The present invention relates to multidentate ligand systems and metal complexes thereof, and to their use in diagnostics and therapy.

BACKGROUND OF THE INVENTION $^{89}$Zr is a metallic radionuclide with promising characteristics for application in medical diagnosis. For in vivo diagnostics or therapeutic applications where radio-labelled compositions are employed, it is important that the radionuclide specifically localizes to target tissues. To provide specific binding to, or absorption by, the particular cells or tissue(s) of interest, radionuclides are generally coupled to targeting agents. Typically, metallic radionuclides are bound to a chelating agent, and the chelating agent is coupled to a targeting moiety, which provides the radiolabelled composition with the ability to bind selectively to a specific population of target cells or tissue(s).

$^{89}$Zr radiolabelled compounds may be employed in a variety of techniques, including PET (positron emission tomography) diagnostics, in particular in the field of immuno-PET, where antibody-based radiotracers are used to image tumours based on the expression of tumour-associated antigens on tumour cells. Radionuclides with suitable half-lives are often employed in nuclear medicine. The half-live of $^{89}$Zr, which is 78.4 h, matches the biological half-lives of antibodies. This makes $^{89}$Zr a favourable radio-metal for application in immuno-PET, which often requires imaging at late time points due to slow accumulation (e.g. several days) of the radioconjugate in the target tissue.

Besides PET radionuclides such as $^{89}$Zr, $^{44}$Sc, $^{64}$Cu, and $^{68}$Ga, gamma ray emitting metallic radionuclides such as $^{67}$Ga, $^{111}$In, or $^{99m}$Tc may also be employed for imaging studies in immunodiagnostics, particularly in single-photon emission computed tomography (SPECT). In addition, particle emitting radionuclides such as $^{177}$Lu, $^{90}$Y or $^{213}$Bi may be employed in therapeutic applications.

Chelation describes a process in which a metal ion or a pre-complexed form thereof, reacts with a chelating agent to form a coordinated chelate complex, in which the metal is coordinatively bound to the chelating agent at two or more sites. The sequestration properties of chelating agents are not only exploited in nuclear medicine in form of radiopharmaceuticals, but also in detoxification techniques. It may also be applied to the development of MRI contrast agent based on gadolinium (Gd) or iron (Fe).

Desferrioxamine (DFO, CAS No. 70-51-9) is a hexadentate chelator, which is clinically approved for the treatment of iron poisoning. $^{89}$Zr has been conjugated to a functionalized derivative of DFO (Fischer et al. *Molecules* 2013, 18, 6469-6490). DFO coordinates only six of the eight available coordination sites of the metal atom, while water molecules occupy the remaining positions. The inability of DFO to bind all coordination sites of $Zr^{4+}$ results in an unfavourable stability of the complex in vivo. Dissociation of $^{89}$Zr from the conjugate in vivo results in its accumulation in radiation sensitive tissue (red bone marrow, specifically). Such unspecific deposition of radioactivity in vivo poses serious limitations to $^{89}$Zr-based radiopharmaceuticals for clinical applications due to the radiation burden to the patients.

The objective of the present invention is to provide improved means for delivering radio-nuclides, particularly $^{67}$Ga, $^{68}$Ga, $^{89}$Zr, $^{177}$Lu, and $^{90}$Y, for diagnostics and/or therapeutic use. This objective is attained by the subject-matter of the independent claims.

Terms and Definitions

Amino acid sequences are given from amino to carboxyl terminus. Capital letters for sequence positions refer to L-amino acids in the one-letter code (Stryer, Biochemistry, 3$^{rd}$ ed. p. 21).

A $C_1$-$C_4$ alkyl in the context of the present specification signifies a saturated linear or branched hydrocarbon having 1, 2, 3 or 4 carbon atoms, wherein one carbon-carbon bond may be unsaturated and one $CH_2$ moiety may be exchanged for oxygen, sulphur or nitrogen (an ether, thioether, sulfoxide, sulfone or amine bridge). Non-limiting examples for a $C_1$-$C_4$ alkyl are methyl, ethyl, propyl, prop-2-enyl, n-butyl, 2-methylpropyl, tert-butyl, but-3-enyl, prop-2-inyl and but-3-inyl.

A $C_1$-$C_5$ alkyl in the context of the present specification signifies a saturated linear or branched hydrocarbon having 1, 2, 3, 4 or 5 carbon atoms, wherein one carbon-carbon bond may be unsaturated and one $CH_2$ moiety may be exchanged for oxygen, sulphur or nitrogen (an ether, thioether, sulfoxide, sulfone or amine bridge). Non-limiting examples for a $C_1$-$C_5$ alkyl include the examples given for $C_1$-$C_4$ alkyl above, and additionally 3-methylbut-2-enyl, 2-methylbut-3-enyl, 3-methylbut-3-enyl, n-pentyl, 2-methylbutyl, 3-methylbutyl, 1,1-dimethylpropyl, 1,2-dimethylpropyl, 1,2-dimethylpropyl and pent-4-inyl.

A $C_1$-$C_8$ alkyl in the context of the present specification signifies a saturated linear or branched hydrocarbon having from one to 8 carbon atoms and includes the definitions for $C_1$-$C_4$ alkyl and $C_1$-$C_5$ alkyl given above.

A saturated alkyl is an alkyl having only saturated carbon-carbon bonds. A partially unsaturated alkyl is an alkyl comprising isolated or conjugated carbon-carbon double bonds, but not aromatic double bonds.

The term arene (or: "aryl") in the context of the present specification signifies a cyclic aromatic $C_5$-$C_{10}$ hydrocarbon. Examples of arene include, without being restricted to, phenyl, naphtyl and heteroarene. A heteroarene ("heteroaryl") in the context of the present invention is an arene that comprises one or several nitrogen, oxygen, and/or sulphur atoms as part of the aromatic system. Examples for heteroarene include, without being restricted to, pyrrole, thiophene, furan, imidazole, pyrazole, thiazole, oxazole, pyridine, thiazine, quinolone, benzofuran and indole. An arene or a heteroarene in the context of the invention additionally may be substituted by one or more alkyl groups. In certain preferred embodiments, the heteroarene is unsubstituted.

The term "substituted" refers to the addition of a substituent group to a parent compound.

"Substituent groups" can be protected or unprotected and can be added to one available site or to many available sites in a parent compound.

"Protected" substituent groups are reactive substituent groups such as a hydroxyl group, an amine or sulfhydryl group, a carboxylic acid group or an carboxylic acid amide group within an organic molecule, which are derivatized to the effect of decreasing their reactivity during a conversion step of the organic molecule, while retaining the ability to restore the substituent group readily by cleavage of the protecting group. Protecting groups and their use are reviewed in Wuts, Greene's protective groups in organic synthesis, Wiley 5th edition 2014 (ISBN 978-1118057483).

Substituent groups may also be further substituted with other substituent groups and may be attached directly or by a linking group such as an alkyl or hydrocarbyl group to a parent compound. "Substituent groups" amenable herein include, without limitation, halogen, oxygen, nitrogen, sulphur, hydroxyl, alkyl, alkenyl, alkynyl, acyl (—C(O)R$^a$), carboxyl (—C(O)OR$^a$), aliphatic groups, alicyclic groups, alkoxy, substituted oxy (—OR$^a$), aryl, aralkyl, heterocyclic radical, heteroaryl, heteroarylalkyl, amino (—N(R$^b$)(R$^c$)), imino (=NR$^b$), amido (—C(O)N(R$^b$)(R$^c$) or —N(R$^b$)C(O)R$^a$), hydrazine derivates (—C(NH)NR$^a$R$^b$), tetrazole (CN$_4$H$_2$), azido (—N$_3$), nitro (—NO$_2$), cyano (—CN), isocyano (—NC), cyanato (—OCN), isocyanato (—NCO), thiocyanato (—SCN); isothiocyanato (—NCS); carbamido (—OC(O)N(R$^b$)(R$^c$) or —N(R$^b$)C(O)OR$^a$), thiol (—SR$^b$), sulfinyl (—S(O)R$^b$), sulfonyl (—S(O)$_2$R$^b$), sulfonamidyl (—S(O)$_2$N(R$^b$)(R$^c$) or —N(R$^b$)S(O)$_2$R$^b$) and fluorinated compounds —CF$_3$, —OCF$_3$, —SCF$_3$, —SOCF$_3$ or —SO$_2$CF$_3$, wherein each R$^a$, R$^b$ and R$^c$ is, independently, H or a further substituent group with a preferred list including without limitation, H, alkyl, alkenyl, alkynyl, aliphatic, alkoxy, acyl, aryl, heteroaryl, alicyclic, heterocyclic and heteroarylalkyl.

An unsubstituted linker chain is a chain constituted only of a linear chain of linker atoms N (nitrogen), C (carbon) and O (oxygen), bound to hydrogen atoms where appropriate. Non-limiting examples are methylene (—CH$_2$—), ethyl (—CH$_2$CH$_2$—) or ethoxyethyl (—CH$_2$CH$_2$—O—CH$_2$CH$_2$—) linker.

A substituted linker chain is a chain constituted of a linear chain of linker atoms N (nitrogen), C (carbon) and O (oxygen), wherein some or all linker atoms are bound to substitute moieties as defined above.

Identity in the context of the present specification is a single quantitative parameter representing the result of a sequence comparison position by position. Methods of sequence comparison are known in the art; the BLAST algorithm available publicly is an example.

SUMMARY OF THE INVENTION

The present invention relates to a ligand able to coordinate Zirconium ions and other related metal ions by four hydroxamate groups, wherein the hydroxamate moieties are spaced by between 9 and 12 bonds, particularly 10 bonds, in other words the hydroxamates are separated by linkers having between 8 and 11, particularly 9 carbon or hetero atoms between them. The ligand is attached, or attachable, covalently to a moiety conferring targeting specificity onto the ligand. The moiety conferring targeting specificity may be an antibody or a ligand for a tissue-specific receptor.

The invention further relates to a complex between the ligand of the invention, and a metal atom coordinated by the ligand.

The invention further relates to the use of such complex in diagnosis or therapy of disease.

DETAILED DESCRIPTION OF THE INVENTION

According to a first aspect of the invention, a ligand characterized by a general formula I:

R$^1$-D-X-D-X-D-X-D-E-R$^2$     (I)

is provided, wherein
each D is a hydroxamate moiety, each X is a spacer separating two hydroxamate moieties, R$^1$ is a non-reactive terminal moiety, R$^2$ is a moiety conferring tissue specificity or the ability to link the molecule to a tissue specific moiety, and E is an optional spacer separating the ligand and R$^2$.

In particular,

D is C(O)N(OH)

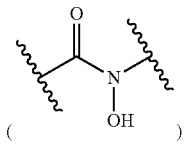 [SMILES: *C(=O)N(*)O]

or N(OH)C(O)

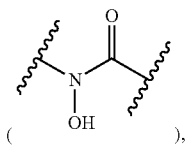

or

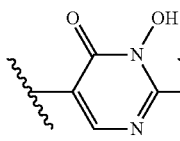 or 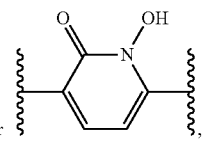

each X independently of any other X is a saturated or partially unsaturated, substituted or unsubstituted linker comprising a chain of 8, 9, 10 or 11, in certain embodiments particularly 9, atoms selected from any of N, C and O, R$^1$ is or comprises H, a C$_1$-C$_5$ alkyl, a C$_3$-C$_6$ cycloalkyl, an arene, and/or a heteroarene;

E is a saturated or partially unsaturated, substituted or unsubstituted linker comprising a chain of 1-50 atoms and R$^2$ is a) an OH, NH$_2$, SH, COOH, CHO, N$_3$, SCN, CH$_2$X (X=Cl, Br, I), activated ester (e.g., NHS, tetra- or pentafluoro phenol derivatives), an ene-one-system (alpha, beta unsaturated carbonyl, a Michael acceptor system (e.g., maleimide)) a diene/dienophile (Diels Alder), an alkene, or an alkyne, b) a first click moiety capable of selectively forming a covalent bond with a second click moiety R$^3$ under reaction conditions not leading to a covalent reaction of R$^2$ or R$^3$ with natural occurring polypeptides, in particular with proteins, or c) an antibody, an oligopeptide, a polypeptide, a polynucleotide, a liposome, a polymerosome, a phospholipid, a vitamin, a monosaccharide, an oligosaccharide, a nanoparticle, or a drug-like molecule having a molecular weight less than (<) 3000 U, or a moiety that specifically binds to a target site on cells and/or tissues with an association constant of lower than (<) $10^{-6}$ mol/l, $<10^{-7}$ mol/l, $<10^{-8}$ mol/l or $<10^{-9}$ mol/l, or d) a solid support.

In certain embodiments, D is a substituted or unsubstituted pyrimidinone or pyridinone moiety.

In certain embodiments, X is a saturated or partially unsaturated, substituted or unsubstituted linker comprising 8, 9, 10, or 11 atoms, particularly 9 atoms within the chain (the counted atoms constituting the chain backbone; i.e. an ethyl group $\underline{CH_2}$—$\underline{CH_2}$ counts as two atoms; the chains —$\underline{C}(O)\underline{N}H\underline{C}H_2\underline{C}H_2\underline{C}H_2$— and —$\underline{C}(O)\underline{N}H\underline{C}H(CH_3)\underline{C}H_2$ $\underline{C}H_2$— both count as 5 atoms; counted atoms are underlined) selected from $CH_2$, NR, CO and O, with R being H or $C_1$-$C_4$ alkyl. In certain embodiments, R is H.

In certain embodiments, X is unsubstituted. In certain embodiments, X is an unsubstituted linear chain consisting of $C_1$-$C_5$ alkyl moieties bridged (linked) by COO (ester) or CONH (amide) moieties. In certain embodiments, each X independently of any other X is a saturated or unsaturated, substituted or unsubstituted heterocyclic moiety.

In certain embodiments, each X independently of any other X is a linker defined by the structure —$(CH_2)_k$—Y—$(CH_2)_m$—Y—$(CH_2)_n$—Y—$(CH_2)_p$—, wherein each Y independently of any other Y can be an ether bridge (—O—), an amine bridge (—NH— or —NCH$_3$—), an amide bridge in either orientation (—CO—NH—, or —HN—CO—), or an ester bridge in either orientation (—COO— or —OCO), with the proviso that the number of covalent links in the linker chain is 7 to 10, in other words, each pair of D moieties is separated by 8, 9, 10 or 11 covalent bonds in the linker moiety X between them.

In certain embodiments, each X independently of any other X is a linker defined by the structure —$(CH_2)_k$—$Y_a$—$(CH_2)_m$—$Y_b$—$(CH_2)_n$—$Y_c$—$(CH_2)_p$—, each Y independently of any other Y is an amide bridge in either orientation (—CO—NH—, or —HN—CO—), or an ester bridge in either orientation (—COO— or —OCO), k, m, n, and p can have values from 0 to 11, a, b and c are either 0 or 1 and the sum of k+m+n+2 (a+b+c) is a number between 8 and 11.

In certain embodiments, $R^1$ is $CH_3$, $CH_2CH_3$, or a saturated or partially unsaturated $C_3$-$C_6$ cyclic alkyl moiety, or a monoanular or bianular aryl or heteroaryl moiety, particularly a saturated or partially unsaturated $C_3$-$C_6$ cyclic alkyl moiety, or a monoanular or bianular aryl or heteroaryl moiety consisting of between three and fifteen carbon or hetero (N, C, O, S) atoms (and hydrogen as appropriate).

In certain embodiments, E is a saturated or partially unsaturated, substituted or unsubstituted linker comprising 2, 3, 4, 5, 6, 7, 8, 9, 10, 11, 12, 13, 14, 15, 20, 5 to 25, 10 to 30, 20 to 50 or 30 to 50 atoms selected from C, O, N and S (the counted atoms constituting the chain backbone and are counted as exemplified for X above). In certain embodiments, E is integral with $R^2$.

In certain embodiments, D is

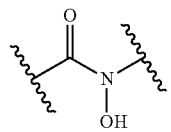 [SMILES: *C(=O)N(*)O]

(in text form: C(O)N(OH)),

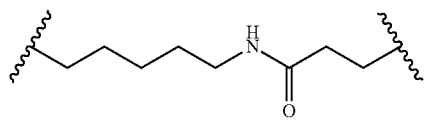 [SMILES: *CCCCCNC(=O)CC*]

each X is (all X are)
$R^1$ is methyl, ethyl or propyl, and
E is $(CH_2)_5NH$—.

In one embodiment, the ligand is characterized by the following formula:

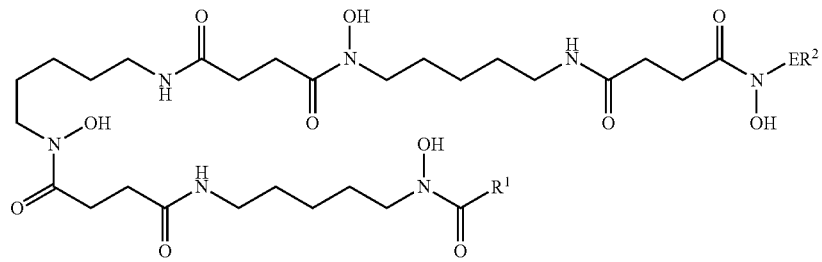

In another embodiment, the ligand is characterized by the following formula:

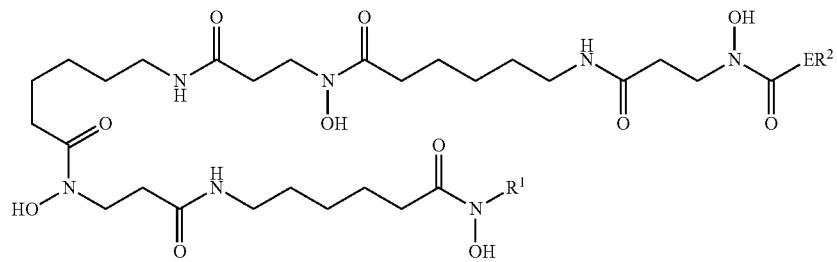

In certain embodiments, $R^2$ comprises, or is, an antibody, an oligopeptide, a polypeptide or protein, a polynucleotide, a liposome, a polymerosome, a phospholipid, a vitamin, a monosaccharide, an oligosaccharide, a nanoparticle, or a drug-like molecule having a molecular mass less than (<) 3000 U, any of which is selective for a disease specific ligand, a cell specific ligand or a tissue specific ligand.

In certain embodiments, $R^2$ is a vitamin selected from folic acid, biotin, retinol, thiamine, riboflavin, niacin, pantothenic acid, pyridoxine, ascorbic acid, cyanocobalamin, cholecalciferol, tocopherol, and phylloquinone.

In certain embodiments, $R^2$ comprises, or is, a biotin molecule. Biotin may be bound to the ligand by conjugation to an amine, sulfhydryl and/or OH via its valeric acid side chain. Non-covalent binding of biotin to avidin or streptavidin, which in turn is covalently linked to a high-specificity ligand such as an antibody, can be employed to enhance the versatility of the ocatadentate ligand of the invention, for example for use in radionuclide-based diagnosis and therapy. In certain embodiments, $R^2$ comprises an avidin or streptavidin molecule conjugated to the ligand allowing for binding non-covalently to biotin-labelled molecules.

In certain embodiments, $R^2$ is an OH, SH, COOH, SCN, activated ester, or an ene-one-system (an alpha, beta unsaturated carbonyl, also referred to as a Michael acceptor system).

In certain embodiments, $R^2$ comprises, or is, one partner of two partners forming a so-called click reaction couple. In such embodiments, $R^2$ is a first click moiety capable of forming a covalent bond selectively with a second click moiety $R^3$ under reaction conditions not leading to a covalent reaction of $R^2$ or $R^3$ with natural occurring polypeptides, in particular with proteins. The click reactive groups are meant to conjugate the ligand to molecules of interest and at the same time provide the possibility of novel pre-targeting approaches. In certain embodiments, $R^2$ is selected from an azide, an alkyne, a tetrazine, a cyclooctine and a trans-cyclooctene, Suitable click reaction partners are well known in the art.

In certain embodiments, $R^2$ comprises, or is, a drug like moiety having a molecular mass of more then 160 u but less than 1000 u, less than 700 u, or less than 500 u, comprises up to five hydrogen bond donators (e.g., oxygen and or nitrogen atoms with one H attached), up to ten hydrogen bond acceptors (e.g., oxygen or nitrogen atoms) and an octanol-water partition coefficient log P of below 5.6 (any of these characteristics applied to the isolated $R^2$ moiety, without regard to the rest of compound I). These are the so-called "Lipinski" rules of 5 (originally, referring to molecules between 160 and 500 u) for drug-like compounds.

In certain embodiments, $R^2$ comprises, or is, an antibody, an antibody fragment, an antibody-like molecule, an oligopeptide or a nucleic acid aptamer molecule of 10 to 75 nucleotides in length, capable of binding to a cell specific or tissue specific target, particularly a cancer specific target.

An antibody fragment may be a Fab domain or an Fv domain of an antibody, or a single-chain antibody fragment, which is a fusion protein consisting of the variable regions of light and heavy chains of an antibody connected by a peptide linker. The $R^2$ moiety may also be a single domain antibody, consisting of an isolated variable domain from a heavy or light chain. Additionally, an antibody may also be a heavy-chain antibody consisting of only heavy chains such as antibodies found in camelids. An antibody-like molecule may be a repeat protein, such as a designed ankyrin repeat protein (Molecular Partners, Zürich).

Methods for generating antibodies against cell specific or tissue specific targets are known in the art. They include, for example, immunization of mice with human isolated targets, or immunization of mice with expression vectors encoding the target (DNA immunization).

Suitable $R^2$ moieties according to the above aspect of the invention may also be developed by evolutive methods such as phage display, ribosome display or SELEX, wherein polypeptides or oligonucleotides are selected due to their binding affinity to a target of interest. Additionally, the binding affinity of an identified $R^2$ moiety may be improved by cycles of evolution of the amino acid sequence or nucleotide sequence and selection of the evolved $R^2$ moiety may be effected based on the required affinity.

In embodiments where $R^2$ comprises an oligopeptide, $R^2$ may be a peptide that can bind to a recognition site of a receptor situated on the surface of a tissue-specific cell.

Alternatively, $R^2$ may comprise a soluble polypeptide comprising a contiguous amino acid sequence of at least 8 amino acid residues taken from the protein sequence of a soluble polypeptide ligand of a cell- or tissue specific receptor, wherein said soluble polypeptide binds to said receptor with a dissociation constant of $10^{-6}$ mol/l or lower, particularly with a dissociation constant of $\leq 10^{-8}$ mol/l.

In certain embodiments, $R^2$ comprises, or is, a monosaccharide consisting of three to seven carbon atoms. Examples are glyceraldehyde (C3), erythrose or threose (C4), arabinose, ribose or xylose (C5) glucose, mannose, galactose or fructose (C6) or sedoheptulose (C7). The sugar alcohols and amino sugars of C3 to C7 monosaccharides are included in the group of monosaccharides according to the definition used herein.

An oligosaccharide is a molecule consisting of two to ten of the same or different monosaccharides according to the above definition. A polysaccharide comprises more than ten monosaccharides.

In certain embodiments, $R^2$ comprises, or is, a vesicle-like molecule enclosing a solution comprising nutrients and/or drugs, which is used for administration of said nutrients and/or drugs (see Mishra et al., Journal of Biomedical Materials Research, Part A (2013), 101A(12), 3646-3660).

In certain embodiments, $R^2$ comprises, or is, a lipid structure with amphipathic character used as vesicular carrier for enhanced delivery of nutrients and/or drugs, thereby improving bioavailability and reducing toxicity.

In certain embodiments, $R^2$ is an alkyne or azide moiety, an alkyne, a tetrazine, a cyclooctine, a trans-cyclooctene, a carboxy group, an amino group, iodine, bromine, chlorine, succinimide, thiol group, a cyclooctyne moiety, biotin, avidin, or streptavidin.

In certain embodiments, $R^2$ is a nanomaterial, more particularly a nanoparticle. Nanoparticles may be selected from gold, silica, lipids, polymeric, metal or metal oxide compositions, wherein said metals are selected from iron, manganese, or titanium. The sizes of nanoparticles cover a range between 1 and 500 nanometers. They have unique physicochemical properties due to their large surface area to mass ratio and high activity, which differs from bulk materials of the same composition. For diagnostic and therapeutic applications, nanoparticles may be covalently linked to amino acids, antibodies, aptamers, avidin, streptavidin, peptides, polypeptides, polynucleotides, and/or nucleotides, which specifically bind to their biological targets. Drug-coated or liposomal nanoparticles may be used as carrier particles for targeted drug delivery. Metal oxide nanoparticles conjugated to radioisotopes enable monitoring of their biodistribution in vivo.

"Nucleotides" in the context of the present specification are nucleic acid or nucleic acid analogue building blocks, oligomers of which are capable of forming selective hybrids with DNA or RNA oligomers or artificial nucleic acid oligomers on the basis of base pairing. The term nucleotides in this context includes the classic ribonucleotide building blocks adenosine, guanosine, uridine (and ribosylthymin), cytidine, the classic deoxyribonucleotides deoxyadenosine, deoxyguanosine, thymidine, deoxyuridine and deoxycytidine. It further includes analogues of nucleic acids such as phosphotioates, 2'O-methylphosphothioates, peptide nucleic acids (PNA; N-(2-aminoethyl)-glycine units linked by peptide linkage, with the nucleobase attached to the alpha-carbon of the glycine) or locked nucleic acids (LNA; 2'O, 4'C methylene bridged RNA building blocks). The hybridizing sequence may be composed of any of the above nucleotides, or mixtures thereof.

Targeting Moieties:

In certain embodiments, $R^2$ is bombesin (CAS No. 31362-50-2). In certain embodiments, $R^2$ comprises a functional homologue of bombesin, having an amino acid sequence of at least 80%, 85%, 90%, 95%, 98%, 99% identity to SEQ ID NO 1 (bombesin)

SEQ ID NO 1:
QQRLGNQWAVGHLM

In certain embodiments, $R^2$ is somatostatin (CAS No. 38916-34-6). In certain embodiments, $R^2$ comprises a functional homologue of somatostatin, having an amino acid sequence of at least 80%, 85%, 90%, 95%, 98%, 99% identity to SEQ ID NO 2 (somatostatin).

SEQ ID NO 2:
MLSCRLQCALAALSIVLALGCVTGAPSDPRLRQFLQKSLAAAAGKQELAK
YFLAELLSEPNQTENDALEPEDLSQAAEQDEMRLELQRSANSNPAMAPRE
RKAGCKNFFWKTFTSC

In certain embodiments, $R^2$ is gastrin (UniProt ID: P01350). In certain embodiments, $R^2$ comprises a functional homologue of gastrin, having an amino acid sequence of at least 80%, 85%, 90%, 95%, 98%, 99% identity to SEQ ID NO 3 (gastrin).

SEQ ID NO 3:
MQRLCVYVLIFALALAAFSEASWKPRSQQPDAPLGTGANRDLELPWLEQQ
GPASHHRRQLGPQGPPHLVADPSKKQGPWLEEEEEAYGWMDFGRRSAEDE
N

In certain embodiments, $R^2$ comprises a peptide sequence of trans-activator of transcription protein (tat) (Pfam ID: PF00539). In certain embodiments, $R^2$ comprises the amino acid sequence of the protein transduction domain identical to SEQ ID NO 4 (tat peptide transduction domain).

SEQ ID NO 4:
YGRKKRRQRRR

In certain embodiments, $R^2$ is prostate-specific antigen (PSA) (UniProt ID: P07288). In certain embodiments, $R^2$ comprises a functional homologue of PSA, having an amino acid sequence of at least 80%, 85%, 90%, 95%, 98%, 99% identity to SEQ ID NO 5 (PSA).

SEQ ID NO 5:
MWVPVVFLTLSVTWIGAAPLILSRIVGGWECEKHSQPWQVLVASRGRAVC
GGVLVHPQWVLTAAHCIRNKSVILLGRHSLFHPEDTGQVFQVSHSFPHPL
YDMSLLKNRFLRPGDDSSHDLMLLRLSEPAELTDAVKVMDLPTQEPALGT
TCYASGWGSIEPEEFLTPKKLQCVDLHVISNDVCAQVHPQKVTKFMLCAG
RWTGGKSTCSGDSGGPLVCNGVLQGITSWGSEPCALPERPSLYTKVVHYR
KWIKDTIVANP

In certain embodiments, $R^2$ is neuropeptide Y (NPY) (UniProt ID: P01303). In certain embodiments, $R^2$ comprises a functional homologue of NPY, having an amino acid sequence of at least 80%, 85%, 90%, 95%, 98%, 99% identity to SEQ ID NO 6 (NPY).

SEQ ID NO 6:
MLGNKRLGLSGLTLALSLLVCLGALAEAYPSKPDNPGEDAPAEDMARYY
SALRHYINLITRQRYGKRSSPETLISDLLMRESTENVPRTRLEDPAMW

In certain embodiments, $R^2$ is octreotide (CAS No. 83150-76-9), also known as "Sandostatin" (Novartis Pharmaceuticals), identical to SEQ NO 7. Octreotide is an octapeptide that pharmacologically mimics natural somatostatin, though it is a more potent inhibitor of growth hormone, glucagon, and insulin than somatostatin.

SEQ ID NO 7:
FCFWKYCT-ol (Disulfide bridge: 2-7)

In certain embodiments, $R^2$ is gastric inhibitory polypeptide (GIP) (UniProt ID: P09681). In certain embodiments, $R^2$ comprises a functional homologue of GIP, having an amino acid sequence of at least 80%, 85%, 90%, 95%, 98%, 99% identity to SEQ ID NO 8 (GIP).

SEQ ID NO 8:
MVATKTFALLLLSLFLAVGLGEKKEGHFSALPSLPVGSHAKVSSPQPRG
PRYAEGTFISDYSIAMDKIHQQDFVNWLLAQKGKKNDWKHNITQREARA
LELASQANRKEEEAVEPQSSPAKNPSDEDLLRDLLIQELLACLLDQTNL
CRLRSR

In certain embodiments, $R^2$ is neurokinin A (NKA) (UniProt ID: P20366). In certain embodiments, $R^2$ comprises a functional homologue of NKA, having an amino acid sequence of at least 80%, 85%, 90%, 95%, 98%, 99% identity to SEQ ID NO 9 (NKA).

SEQ ID NO 9:
MKILVALAVFFLVSTQLFAEEIGANDDLNYWSDWYDSDQIKEELPEPFE
HLLQRIARRPKPQQFFGLMGKRDADSSIEKQVALLKALYGHGQISHKRH
KTDSFVGLMGKRALNSVAYERSAMQNYERRR

In certain embodiments, $R^2$ is neurotensin (UniPro ID: P30990). In certain embodiments, $R^2$ comprises a functional homologue of neurotensin, having an amino acid sequence of at least 80%, 85%, 90%, 95%, 98%, 99% identity to SEQ ID NO 10 (NKA).

SEQ ID NO 10:
MMAGMKIQLVCMLLLAFSSWSLCSDSEEEMKALEADFLTNMHTSKISKA
HVPSWKMTLLNVCSLVNNLNSPAEETGEVHEEELVARRKLPTALDGFSL
EAMLTIYQLHKICHSRAFQHWELIQEDILDTGNDKNGKEEVIKRKIPYI
LKRQLYENKPRRPYILKRDSYYY

In certain embodiments, $R_2$ is exendin-3 (CAS No. 130357-25-4). In certain embodiments, $R_2$ comprises a functional homologue of exendin-3, having an amino acid sequence of at least 80%, 85%, 90%, 95%, 98%, 99% identity to SEQ ID NO 11 (exendin-3).

```
SEQ ID NO 11:
HGGGTFTSDLSKQMEEEAVRLFIEWLKNGGPSSGAPPPS-NH₂
```

In certain embodiments, $R^2$ is exendin-4 (CAS No. 141758-74-9). In certain embodiments, $R^2$ comprises a functional homologue of exendin-4, having an amino acid sequence of at least 80%, 85%, 90%, 95%, 98%, 99% identity to SEQ ID NO 12 (exendin-4).

```
SEQ ID NO 12:
HGEGTFTSDLSKQMEEEAVRLFIEWLKNGGPSSGAPPPS-NH₂
```

In certain embodiments, $R^2$ is substance P (SP) comprising the amino acid sequence identical to SEQ ID NO 13 (substance P).

```
SEQ ID NO 13:
RPKPQQFFGLM
```

According to a second aspect of the invention, a compound formed by complex formation between the ligand according to the first aspect of the invention and a metal atom is provided. The metal atom is coordinatively bound to the D moieties of the ligand. In certain embodiments, the metal atom is octa-coordinated, i.e. eight atoms of the ligand collaborate in complex formation with the atom (the coordination number is 8), particularly where the metal is Zr or Y, more particularly where the metal is $^{89}$Zr or $^{90}$Y.

In certain embodiments, the metal atom is hexa-coordinated, i.e. six atoms of the ligand collaborate in complex formation with the atom, particularly where the metal is Ga or In, more particularly where the metal is $^{111}$In, $^{67}$Ga or $^{68}$Ga. In certain embodiments, the metal atom is tetra-coordinated. In certain embodiments, the metal atom is penta-coordinated.

In certain embodiments, the metal has the oxidation number +1, +2, +3, +4, +5, +6, or +7. In certain embodiments, the metal has the oxidation number +3, +4, +5 or +6. In certain embodiments, the metal has a coordination number from 4 to 8.

In certain embodiments, the metal is comprised in any one of the groups 3, 4, 6, 7, 9, 10, 11, 13, 15, the lanthanide group of elements, or the actinide group of elements of the periodic table of the elements. Groups are assigned in accordance to current IUPAC practice, older designations refer to the "scandium group" (IIIA) for group 3, "titanium group" (IVA) for group 4, "actinides group" for group 6, "manganese group" for group 7, "lanthanides group" comprising group, 9, 10, and 11, "boron group" for group 13, and "nitrogen group" for group 15.

In certain embodiments, the metal is selected from zirconium (Zr), yttrium (Y), gallium (Ga), technetium (Tc), indium (In), copper (Cu), terbium (Tb), scandium (Sc), lutetium (Lu), rhenium (Re), bismuth (Bi), europium (Eu), gold (Au), iron (Fe), magnesium (Mg) or gadolinium (Gd).

In certain embodiments, the metal is a metallic radionuclide. A radionuclide, or a radioactive nuclide, is an atom with an unstable nucleus, which undergoes radioactive decay, resulting in the emission of gamma ray(s) or subatomic particles such as positrons, alpha or beta particles, or Auger electrons. These emissions constitute ionizing radiation. Radionuclides occur naturally, or can be produced artificially. Radionuclides are often referred to as radioactive isotopes or radioisotopes.

In certain embodiments, the metal is selected from $^{44}$Sc, $^{64}$Cu, $^{67}$Ga, $^{68}$Ga, $^{89}$Zr, $^{99}$Y, $^{99m}$Tc, $^{111}$In, $^{nat}$Gd, $^{nat}$Eu, $^{177}$Lu, $^{186}$Re, $^{188}$Re, or $^{213}$Bi. In certain embodiments, the metal is $^{67}$Ga, $^{68}$Ga, $^{89}$Zr, or $^{90}$Y.

In certain embodiments, the complex is an octadentate complex and the metal is selected from $^{67}$Ga, $^{68}$Ga, $^{89}$Zr, or $^{90}$Y.

The invention is not limited to octadentate coordinated complexes. In certain embodiments, the complex may comprise Ga or In and may be 6-coordinate. In certain embodiments, the complex may comprise Zr or Y and may be 8-coordinate. In certain embodiments, the complex may comprise Tc and may be 4-coordinate. Even if a metal does not require all coordination sites provided by the ligand system, the ligand will increase the stability of the complex simply by providing higher "concentration" of coordinating groups in the near vicinity of the metal which will protect it from trans-chelation.

According to a third aspect of the invention, a method for the synthesis of a complex according to the second aspect of the invention is provided, wherein a ligand according to the first aspect of the invention is reacted with a metal, particularly a metal of group 3, 4, 6, 7, 9, 10, 11, 13, 15, the lanthanide group of elements, or the actinide group of elements of the periodic table is reacted with the ligand.

In certain embodiments, the complex is formed by providing a ligand according to the invention, and adding a metal. In certain embodiments, the metal is selected from Ga, Tc, In, Cu, Tb, Sc, Lu, Re, Bi, Eu, Gd, Zr, or Y.

In certain embodiments, the metal is selected from the isotopes $^{67}$Ga, $^{68}$Ga, $^{89}$Zr, or $^{90}$Y.

In certain embodiments, the complex is isolated after synthesis by high-performance liquid chromatography (HPLC).

In certain embodiments, an octa co-ordinated complex I (b) is formed by reaction of a ligand I (a) with a metal comprised in any one of the groups 3, 4, 6, 7, 9, 10, 11, 13, or 15 of the periodic table of the elements. In certain embodiments the metal is zirconium. In certain embodiments, said complex I is formed by reaction of said ligand (a) with zirconium chloride ($ZrCl_4$) (CAS No. 10026-11-6). FIG. 2 shows the calculated structure of the octa co-ordinated complex I.

In another embodiment, an octa co-ordinated complex II (d) is formed by reaction of a ligand II (c) with a metal comprised in any one of the groups 3, 4, 6, 7, 9, 10, 11, 13, or 15 of the periodic table of the elements. In certain embodiments the metal is zirconium. In certain embodiments, said complex II is formed by reaction of said ligand II with zirconium (IV) acetylacetonate (CAS No. 10026-11-6).

In yet another embodiment, ligand III (e) is synthesised from a peptide precursor compound. In certain embodiments, said peptide precursor compound is a modified amino acid sequence of bombesin.

```
SEQ ID NO 14:
(β-A)₃-QWAVGHL-14Nle-CONH₂
```

In certain embodiments, complex III is formed by reaction of said ligand III (e) with a metal comprised in any one of groups 3, 4, 6, 7, 9, 10, 11, 13, or 15 of the periodic table of the elements. In certain embodiments the metal is zirconium. In certain embodiments, ligand III is radiolabelled using commercial $^{89}$zirconium oxalate. FIG. 1 shows stability of complex III in comparison to a hexadentate $^{89}$zirconium-complex.

Particular embodiments of this aspect of the invention are:

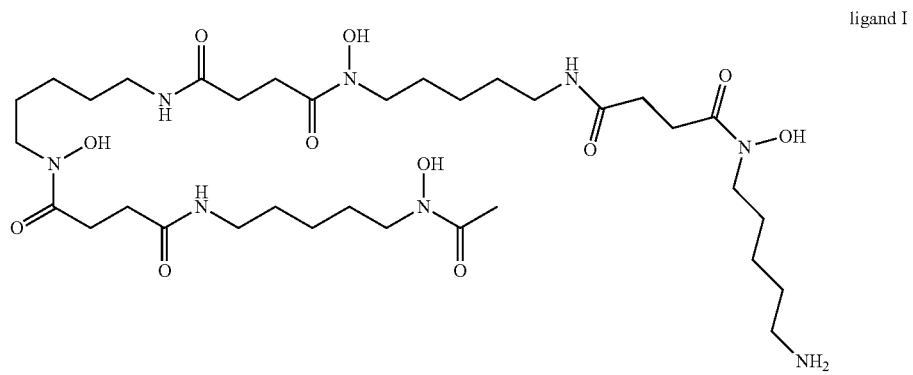 [SMILES: CC(=O)N(O)CCCCCNC(=O)CCC(=O)N(O)CCCCCNC(=O)CCC(=O)N(O)CCCCCNC(=O)CCC(=O)N(O)CCCCCN]
ligand I a. N-[5-[[4-[5-[[4-[5-[acetyl(hydroxy)amino]pentylamino]-4-oxo-butanoyl]-hydroxy-amino]pentylamino]-4-oxo-butanoyl]-hydroxy-amino]pentyl]-N'-(5-aminopentyl)-N'-hydroxy-butanediamide (ligand I) and its Zr complex I:

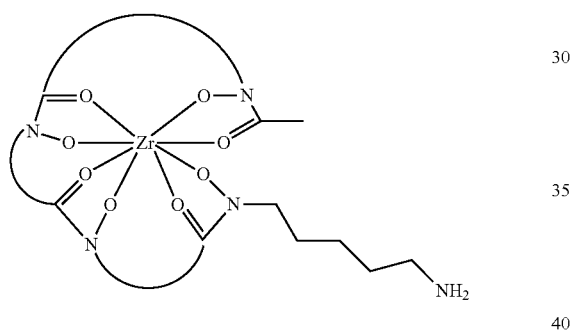
complex I b. Octa co-ordinated complex I

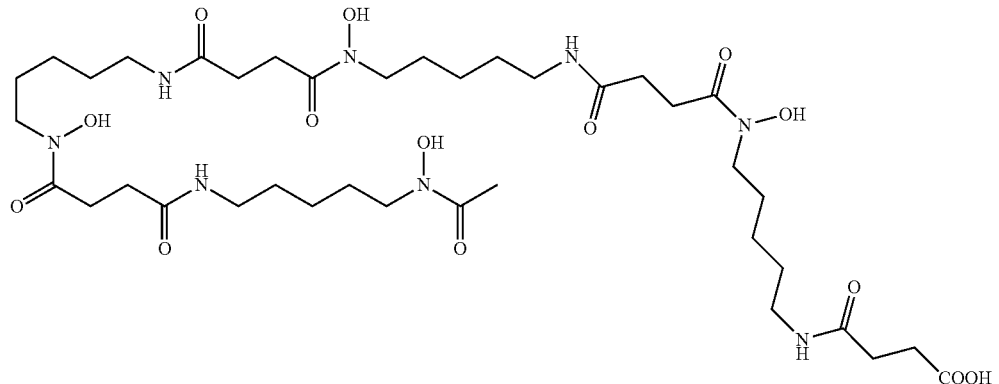
ligand II c. 4-[5-[[4-[5-[[4-[5-[[4-[5-[acetyl(hydroxy)amino]pentylamino]-4-oxo-butanoyl]-hydroxy-amino]pentylamino]-4-oxo-butanoyl]-hydroxy-amino]pentylamino]-4-oxo-butanoyl]-hydroxy-amino]pentylamino]-4-oxo-butanoic acid (ligand II) and its Zr complex II:

complex II
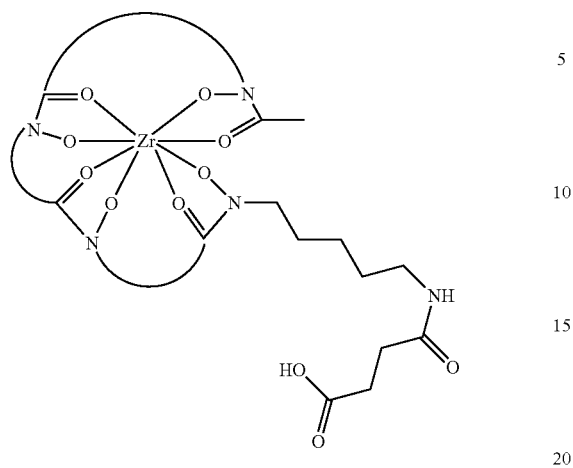
d. Octa co-ordinated complex II

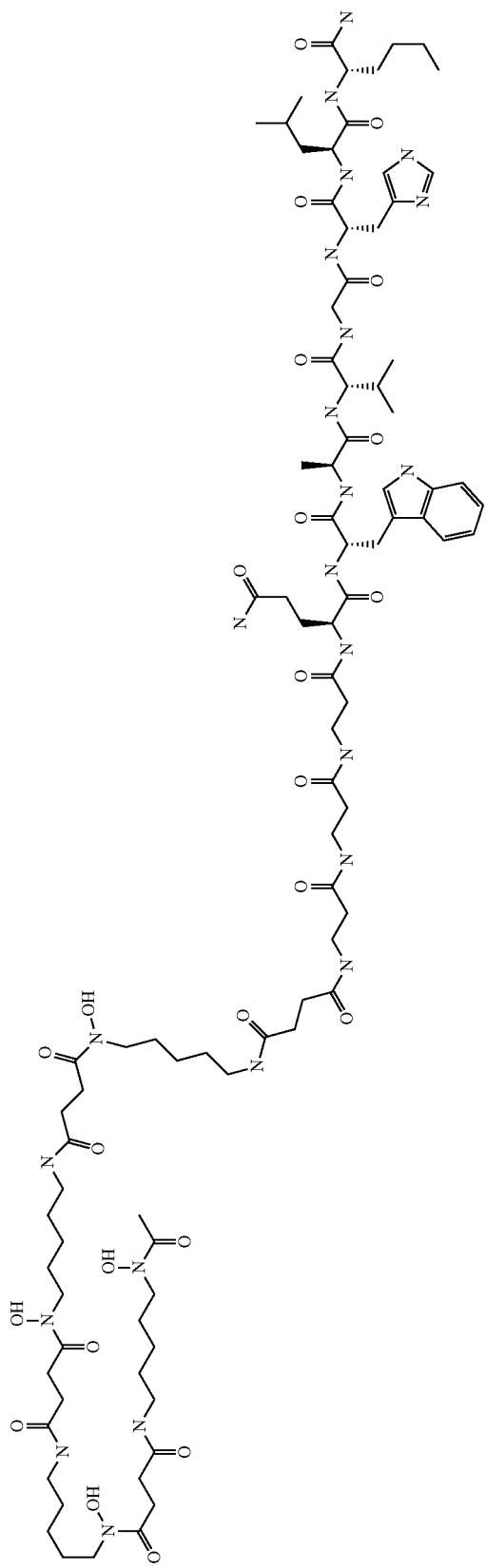

e. (2S)-2-[3-[3-[3-[[4-[5-[[4-[5-[[4-[5-[[4-[5-[acetyl(hydroxy)amino]pentylamino]-4-oxo-butanoyl]-hydroxyamino]pentylamino]-4-oxo-butanoyl]-hydroxy-amino]pentylamino]-4-oxo-butanoyl]-hydroxy-amino]pentylamino]-4-oxo-butanoyl]amino]propanoylamino]propanoylamino]propanoylamino]-N-[(1S)-2-[[(1S)-2-[[1-[[2-[[(1S)-2-[[(1S)-1-[[(1S)-1-carbamoylpentyl]carbamoyl]-3-methyl-butyl]amino]-1-(1H-imidazol-4-ylmethyl)-2-oxo-ethyl]amino]-2-oxo-ethyl]carbamoyl]-2-methyl-propyl]amino]-1-methyl-2-oxo-ethyl]amino]-1-(1H-indol-3-ylmethyl)-2-oxo-ethyl]pentanediamide. (Ligand III)
f. Octa co-ordinated complex III (see structure under Example h).

Other particular embodiments relate to molecules comprising ligand I, II or III complexed to $^{89}$Zr, and covalently linked to any of the above named targeting moieties.

According to an alternative aspect, the invention provides a ligand characterized by the features as outlined in the following items:

Item 1: a ligand characterized by a general formula I:

$R^1$-D-X-D-X-D-X-D-E-$R^2$ (I), wherein
D is

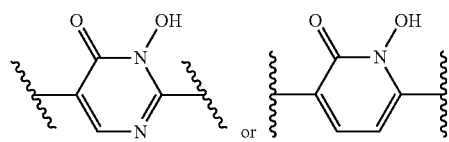 [SMILES: *c1cnc(*)n(O)c1=O ; *c1ccc(*)n(O)c1=O]

each X independently of any other X is a saturated or partially unsaturated, substituted or unsubstituted linker comprising a chain of 2, 3, 4, 5, 6, 7, 8, 9, 10 or 11, in some embodiments particularly 9 atoms selected from any of N, C, O, in particular $CH_2$, NH, CO, O, with R being H or $C_1$-$C_4$ alkyl, or each X independently of any other X is a saturated or unsaturated, substituted or unsubstituted heterocyclic moiety, $R^1$ is or comprises a $C_1$-$C_5$ alkyl, a $C_3$-$C_6$ cycloalkyl, an arene, and/or a heteroarene, E is a saturated or partially unsaturated, substituted or unsubstituted linker comprising a chain comprising 1-50 atoms and $R^2$ is
  a) an OH, SH, COOH, SCN, activated ester, or an ene-one-system;
  b) a first click moiety capable of forming a covalent bond selectively with a second click moiety $R^3$ under reaction conditions not leading to a covalent reaction of $R^2$ or $R^3$ with natural occurring polypeptides, in particular with proteins, or
  c) a targeting moiety that specifically binds to a target site on cells and/or tissues with an association constant of lower than (<) $10^{-6}$ mol/l, <$10^{-7}$ mol/l, <$10^{-8}$ mol/l or <$10^{-9}$ mol/l, particularly an antibody, an oligopeptide, a polypeptide, a polynucleotide, a liposome, a polymerosome, a phospholipid, a vitamin, a monosaccharide, an oligosaccharide, a nanoparticle, or a drug-like molecule having a molecular weight less than (<) 3000 U, or
  d) a solid support.

Item 2: The ligand according to item 1, wherein
$R^2$ is
  i. an alkyne or azide moiety, an alkyne, a tetrazine, a cyclooctine, a trans-cyclooctene, a carboxy group, an amino group, iodine, bromine, chlorine, succinimide, thiol group, a cyclooctyne moiety, biotin, avidin, or streptavidin,
  ii. an antibody, a polypeptide, a polypeptide, a polynucleotide, a liposome, a polymerosome, a phospholipid, a vitamin, a monosaccharide, an oligosaccharide, a nanoparticle, or a drug-like molecule having a molecular weight less than (<) 3000 U;

each X is

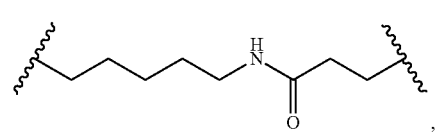 [SMILES: *CCCCCNC(=O)CC*]

$R^1$ is methyl, ethyl or propyl and
E is $(CH_2)_5$—NH—.

Item 3: The ligand according to any one of the above items, wherein $R^2$ comprises a polypeptide being a functional homologue of bombesin, somatostatin, gastrin, transactivator of transcription peptide, prostate-specific antigen, neuropeptide Y, octreotide, gastric inhibitory polypeptide, neurokinin A, neurotensin, exendin-3, exendin-4, or substance P, said peptide comprising an amino acid sequence of at least 80%, 85%, 90%, 95%, 98%, or 99% identity to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, or SEQ ID NO 13, respectively.

Item 4: A complex comprising a ligand according to any one of the above items, coordinatively bound to a metal atom, particularly a metal comprised in group 3, 4, 6, 7, 9, 10, 11, 13, 15, the lanthanide group of elements, or the actinide group of elements of the periodic table.

Item 5: The complex according to item 4, wherein the metal is selected from Ga, Tc, In, Cu, Tb, Sc, Lu, Re, Bi, Eu, Gd, Zr, or Y.

Item 6: The complex according to any one of items 4 or 5, wherein the metal is one of $^{44}$Sc, $^{64}$Cu, $^{67}$Ga, $^{68}$Ga, $^{89}$Zr, $^{90}$Y, $^{99m}$Tc, $^{111}$In, $^{nat}$Eu, $^{nat}$Gd, $^{177}$Lu, $^{161}$Tb, $^{186}$Re, $^{188}$Re, or $^{213}$Bi.

Item 7: The complex according to any one of items 4 to 6, wherein the metal
has the oxidation number +1, +2, +3, +4, +5, +6 or +7, and/or
forms an 8-coordinate complex with the ligand.

Item 8: A complex according to any one of items 4 to 7 for use as a pharmaceutical, particularly for use in a method of treatment of neoplastic disease (cancer).

Item 9: A complex according to any one of items 4 to 7, for use in a method of medical diagnosis or radio-immunotherapy, particularly for use in positron emission tomography and/or single-photon emission computed tomography.

Item 10: A complex according to any one of item 4 to 7 for use in diagnosis of neoplastic disease.

Item 11: A solid support comprising a ligand covalently attached to said solid support, said ligand being characterized by a general formula I $R^1$-D-X-D-X-D-X-D-E-$R^2$ (I)

wherein D is

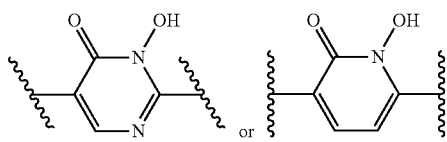

each X independently of any other X is a saturated or partially unsaturated, substituted or unsubstituted linker comprising 2, 3, 4, 5, 6, 7, 8, 9, 10 or 11, in some embodiments particularly 9 atoms selected from any of N, C, O, in particular $CH_2$, NH, CO, O, with R being H or $C_1$-$C_4$ alkyl, or each X independently of any other X is a saturated or unsaturated, substituted or unsubstituted heterocyclic moiety, $R^1$ comprises a $C_1$-$C_5$ alkyl, a $C_3$-$C_6$ cycloalkyl, an arene, and/or a heteroarene, and E is a saturated or partially unsaturated, substituted or unsubstituted chain comprising 1-50 atoms and $R^2$ is the attachment site to said solid support.

Item 12: The solid support according to item 11, wherein said solid support is a nanoparticle.

In certain embodiments, the complex is purified via liquid chromatography, high-performance liquid chromatography (HPLC), size exclusion chromatography (gel permeation chromatography), affinity chromatography, or ion exchange chromatography.

According another aspect of the invention, the complex according to the invention is used as a diagnostic, particularly for cancer diagnostics.

In certain embodiments, the complex is used in radioimmunotherapy.

In certain embodiments, the complex comprising $^{44}$Sc, $^{67}$Ga, $^{68}$Ga, $^{89}$Zr $^{nat}$Eu, and $^{nat}$Gd, $^{nat}$Fe is provided for use in diagnostic imaging, particularly for cancer diagnostics.

In certain embodiments, the complex is used in positron emission tomography or in single-photon emission computed tomography (SPECT or SPET).

In radioimmunotherapy, an antibody or an antibody fragment, which is labelled with a radionuclide, is used to deliver cytotoxic radiation to a target cell or to image a cell for targeting by an external radiation source. In its specific application to cancer therapy, an antibody, which is specific for a tumour-associated antigen, is used to deliver a lethal dose of radiation to the tumour cells or to specifically image radiation dosimetry at the tumour cell. Radioimmunotherapy requires a tumour cell to express an antigen that is unique to the neoplasm or that is not accessible in normal cells.

According another aspect of the invention, the complex according to the invention is used as a pharmaceutical.

In certain embodiments, the complex is used in cancer therapy.

In certain embodiments, the complex is conjugated to receptor-specific molecules comprising an antibody, an oligopeptide, a polypeptide, or a small molecule compound for targeting cancer-type specific receptors and/or receptors overexpressed in certain cancer types.

Breast cancer-specific receptors comprise estrogen/progesterone receptor and human epidermal growth factor 2 receptor (HER2). In certain embodiments, the complex is conjugated to estrogen receptor agonists comprising "indene-based molecules". These molecules have a common "indene" building block as part of their chemical structure. In certain embodiments, the complex is conjugated to molecules selected from 17-beta-estradiol, estrone, raloxifene, estriol, genistein, the monoclonal antibody trastuzumab known as "Herceptin" (Roche), or selective estrogen receptor modulators (SERMs).

Pancreatic cancer and lung cancer are characterised by overexpression of various specific receptors and polypeptides. In certain embodiments, the complex is conjugated to an epidermal growth factor receptor (EGFR)-specific polypeptide or polypeptides comprising epidermal growth factor (EGF), transforming growth factor-alpha (TGF-alpha), the EGFR antagonist potato carboxypeptidase inhibitor (PCI), amphiregulin, insulin-like growth factor 1 (IGF1), or insulin-like growth factor 2 (IGF2). In certain embodiments, the complex is conjugated to compounds comprising gefitinib (CAS No. 184475-35-2), erlotinib (CAS No. 183321-74-6), erlotinib-hydrochloride (CAS No. 183319-69-9), cetuximab (CAS No. 205923-56-4), rituximab or compounds capable of specifically binding to insulin-like growth factor receptors (IGFRs).

Gastric cancer-specific receptors comprise HER2 and CXC chemokine receptors (CXCR1 to CXCR7). In certain embodiments, the complex is conjugated to HER2-specific monoclonal antibodies comprising trastuzumab (CAS No. 180288-69-1) or pertuzumab (CAS No. 380610-27-5). In certain embodiments, the complex is conjugated to CXC chemokine receptor-specific agonists or antagonists.

Prostate cancer development and progression has been shown to correlate with overexpression of androgen receptor (AR) and/or epidermal growth factor receptor (EGFR). In certain embodiments, the complex is conjugated to prostate-specific antigen (PSA) or to an antibody capable of specifically binding to extracellular signal-regulated protein kinases (ERKs). It has also been shown that some prostate cancer types develop and progress independently of androgen receptor signalling. In another embodiment, the complex is conjugated to an antibody capable of specifically binding to B-cell lymphoma 2 (BCL-2) (UniProt ID: P10415) for targeting androgen-independent prostate cancer cells in patients. In certain embodiments, the complex is conjugated to polypeptides or compounds capable of specifically binding to vitronectin receptors (Alpha-v beta-3) (UniProt ID: P04004), selected from angiogenesis inhibitors comprising vitaxin (CAS No. 892553-42-3), or bevacizumab (CAS No. 216974-75-3). In certain embodiments, the complex is conjugated to glycosylated RGD-containing peptides (RGD-peptides) (Haubner et al., *J. Nucl. Med.* 2001, 42(2), 326-336; Zhao et al., *Plos ONE* 8(4), 2013, e61043; Zhang et al., *Cancer Res.* 2007, 67(4), 1555-1562).

Matrix metalloproteinases (MMPs) are zinc-dependent endopeptidases. These enzymes can break down connective tissue and overexpression of MMPs has been observed in pathological conditions comprising inflammation, cancer invasion, metastasis and angiogenesis. In certain embodiments, the complex is conjugated to a matrix metalloproteinase inhibiting compound, in particular an MMP inhibitor selected from the group comprising marimastat (CAS No. 154039-60-8), doxycycline (CAS No. 24390-14-5), or cipemastat (CAS No. 190648-49-8). In certain embodiments, the complex is conjugated to specific tissue inhibitors of metalloproteinases (TIMPs). TIMPs are polypeptides comprising TIMP1, TIMP2, TIMP3, and TIMP4.

Positron emission tomography (PET) is a functional imaging technique applied in nuclear medicine, whereby a three-dimensional image (e.g. of functional processes) in the body is produced. The system detects pairs of gamma rays emitted indirectly by a positron-emitting radionuclide, which is introduced into the body in form of a pharmaceutical compound.

Similar to PET, single-photon emission computed tomography (SPECT) is also applied as a three-dimensional diagnostic imaging technique using gamma rays emitted by radioisotopes. In contrast with PET, the tracer used in SPECT emits gamma radiation that is measured directly, whereas a PET tracer emits positrons that annihilate with near-by electrons, which are a few millimeters away, causing two gamma photons to be emitted in opposite directions. Therefore, PET scanners detect emissions that occur coincidentally in time, thereby providing more radiation event localisation information and thus resulting in higher resolution images compared to SPECT.

Similarly, a dosage form comprising a complex according to the present invention is provided. In certain embodiments, the dosage form is for intravenous administration or subcutaneous administration.

Wherever alternatives for single separable features such as, for example, a metal or radionuclide, ligand element or medical indication are laid out herein as "embodiments", it is to be understood that such alternatives may be combined freely to form discrete embodiments of the invention disclosed herein. Thus, any of the alternative embodiments for a D or X may be combined with any of the alternative embodiments of metal or radionuclide, and these combinations may be combined with any instance of $R^3$ mentioned herein.

The invention is further illustrated by the following examples and figures, from which further embodiments and advantages can be drawn. These examples are meant to illustrate the invention but not to limit its scope.

SHORT DESCRIPTION OF THE FIGURES

FIG. 1 shows a stability profile of the octa co-ordinated complex III (ligand-conjugated complex; top two lines) in comparison to the hexadentate complex known in the art (DFO-conjugated complex; bottom two curves). The graph shows results of competition experiments using 300-fold excess of free DFO in a 24 hour time (Challenging against 0.1 mM DFO-mesylate in 0.5 M HEPES (pH 7.3)). X axis: time; Y axis: percentage of intact complex.

GENERAL METHODS

Figure 1:
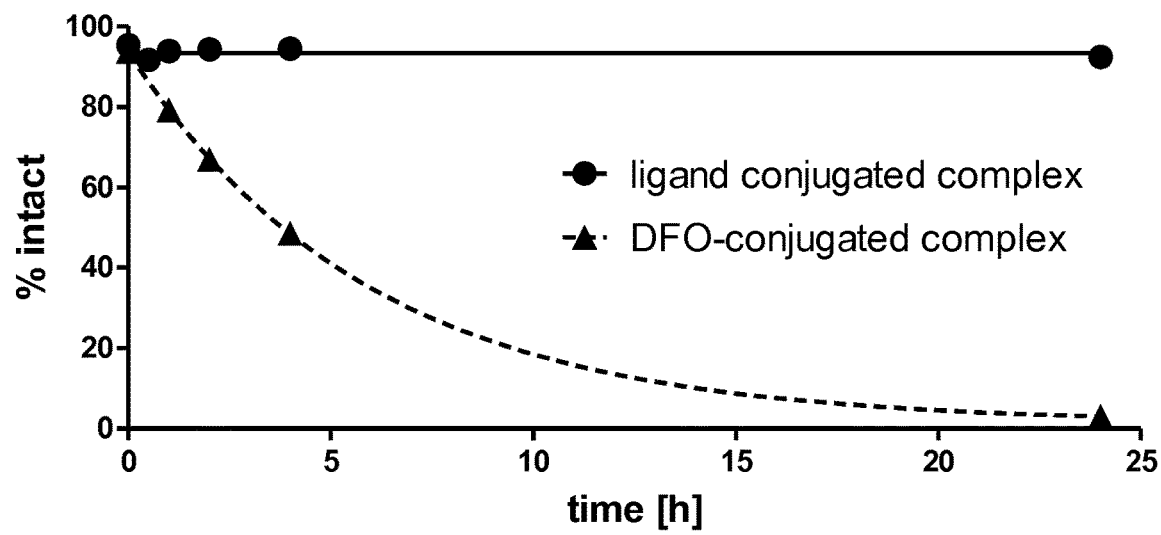
Figure 2:
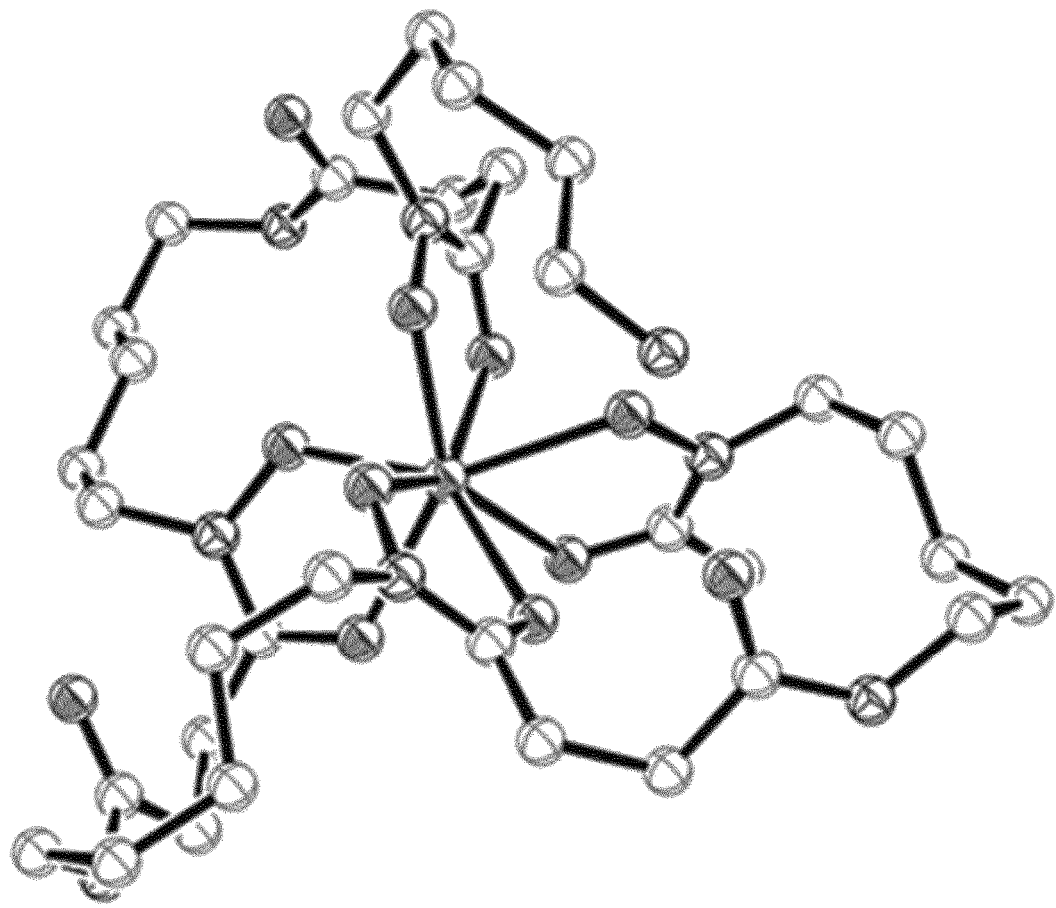
FIG. 2 shows the calculated structure of the complex formed by reaction of ligand I with zirconium chloride. The atoms are depicted in different colours comprising zirconium (center), oxygen (gray), nitrogen (white with bold line), and carbon (white).

Materials:
All chemicals were of reagent grade quality or better, obtained from commercial suppliers and used without further purification. Solvents were used as received or dried over molecular sieves. All preparations were carried out using standard Schlenk techniques.

Instrumentation and Methods:
Instrumentation and Methods. $^1$H and $^{13}$C NMR spectra were recorded in deuterated solvents on 400 ($^1$H: 400 MHz, $^{13}$C: 100.6 MHz) or 500 ($^1$H: 500 MHz, $^{13}$C: 126 MHz) MHz spectrometers at room temperature. The chemical shifts, δ, are reported in ppm (parts per million). The residual solvent peaks have been used as an internal reference. The abbreviations for the peak multiplicities are as follows: s (singlet), d (doublet), dd (doublet of doublets), t (triplet), q (quartet), m (multiplet), and br (broad). The $^1$H and $^{13}$C signals were assigned with the help of 2D NMR techniques. Elemental microanalyses were performed on a LecoCHNS-932 elemental analyser. ESI-MS were performed using a Bruker Daltonics HCT 6000 mass spectrometer. LC-MS spectra were recorded on a HPLC apparatus (Acquity Ultra Performance LC, Waters) that was connected to a mass spectrometer (Bruker Esquire 6000) operated in ESI mode. A Nucleosil 100-5 C18 (250×3 mm) reverse phase column was used with a flow rate of 0.5 mL min$^{-1}$ and UV-absorption was measured at 254 nm. The runs were performed with a linear gradient of A (acetonitrile (Sigma-Aldrich HPLC-grade) and B (distilled water containing 0.02% TFA and 0.05% HCOOH): t=0-3 min, 5% A; t=17 min, 100% A; t=20 min, 100% A; t=21 min, 5% A; t=25 min, 5% A.

Synthesis of the peptide precursor compound characterising a modified amino acid sequence of bombesin (SEQ ID NO. 14) was performed on an Applied Biosystem automatic peptide synthesizer using Rink Amide resin and standard Fmoc-protocoll. Analysis of peptide precursor, ligand I and ligand II were performed on a HPLC system using a Phenomenex Jupiter column, 4μ Proteo 90A, 250×4.6 mm, with a flow rate of 2 mL/min. Analysis of peptide precursor compound and ligand I were performed with a linear gradient of HPLC-grade solvent A (acetonitrile) from Sigma-Aldrich and B (distilled water containing 0.1% TFA). Peptide precursor: t=0 min, 5% A; t=12.5 min, 50% A; t=13.5 min, 95% A; t=14.5 min, 95% A; t=15 min, 5% A; t=17 min, 5% A. Ligand I: t=0 min, 10% A; t=12.5 min, 40% A; t=13.5 min, 95% A; t=14.5 min, 95% A; t=15 min, 10% A; t=17 min, 10% A. Ligand II: t=0 min, 15% A; t=12.5 min, 40% A; t=13.5 min, 95% A; t=14.5 min, 95% A; t=15 min, 15% A; t=17 min, 15% A. MS acquisitions were performed in the full scan mode in the mass range from m/z 100 to 2000 at 20'000 resolution and 1 scan per second. Masses were calibrated with a 2 mmol/l solution of sodium formate over m/z 158 to 1450 mass range with accuracy below 2 ppm.

EXAMPLES a. Synthesis of compound a (4-[benzyloxy-[5-(benzyloxycarbonylamino)pentyl]amino]-4-oxo-butanoic acid) was synthesised following the procedures described in *Na. Chem. Biol.*, 2007, 3, 652-656, and *Na. Chem. Biol.*, 2007, 3, 652-656

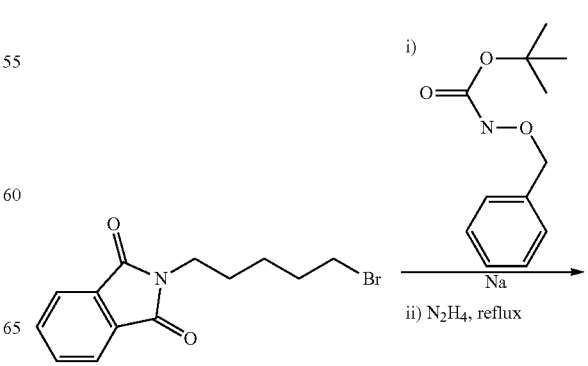

-continued

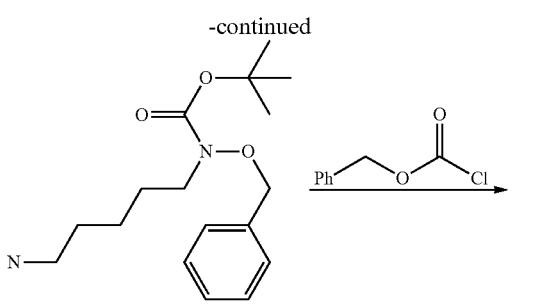

t-butyl N-benzyloxy-N-[5-(benzyloxycarbonylamino)pentyl]carbamate

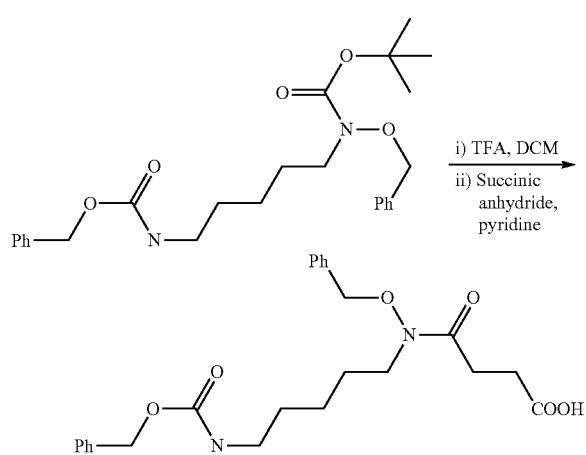

b. Synthesis of Compound b [(benzyl N-[5-[[4-[5-[[4-[5-[[4-[5-[acetyl(hydroxy)amino]pentylamino]-4-oxo-butanoyl]-hydroxy-amino]pentylamino]-4-oxo-butanoyl]-hydroxy-amino]pentylamino]-4-oxo-butanoyl]-benzyloxy-amino]pentyl]carbamate)]

To a stirred solution of carboxylic acid (1.13 g, 2.6 mmol), addition of HATU (1.46 g, 3.8 mmol) in DMF (10 mL), and DIPEA (0.66 g, 5.1 mmol) was carried out under $N_2$ atmosphere. After stirring the mixture for 40 min at room temperature, deferoxamine mesylate salt (1.68 g, 2.6 mmol) followed by DIPEA (0.66 g, 5.1 mmol) and 4-methyl morpholine (2 mL) were added. The mixture was then stirred for 48 h at room temperature. The solvent was removed using a high vacuum pump. Addition of 50 mL ice cold acetone to the resulting paste resulted in a white solid, which was isolated by centrifugation, followed by decantation of the acetone. This procedure was repeated twice. Then a similar washing procedure was followed using double distilled water instead of acetone (3×30 mL). The wet white solid was lyophilized to give result to a white powder.

Data: 1H NMR (400 MHz, DMSO-d6): δ (ppm) 1.16-1.27 (m, 8H), 1.32-1.43 (m, 8H), 1.41-1.56 (m, 8H), 1.97 (s, 3H), 2.24-2.33 (m, 6H), 2.54-2.65 (m, 6H), 2.94-3.03 (m, 8H), 3.43-3.48 (m, 6H), 3.53-3.58 (m, 2H), 4.87 (s, 2H), 4.99 (s, 2H), 7.17-7.47 (m, 11H), 7.76 (s, br, 3H), 9.56-9.67 (m, 3H). 13C{1H} NMR (100 MHz, DMSO-d6): δ (ppm) 20.8, 23.8, 23.9, 26.5, 26.6, 27.7, 28.1, 29.3, 29.4, 30.1, 30.4, 38.9, 45.1, 47.3, 47.6, 65.5, 75.9, 128.2, 128.7, 128.9, 129.1, 129.7, 135.4, 137.8, 156.8, 170.6, 171.4, 171.7, 172.4. ESI-MS (positive detection mode): m/z (%) 1007.3 (100) [M+Na]+. Anal. Calcd for $C_{49}H_{76}N_8O_{13}$: C, 59.74, H, 7.78, N, 11.37. Found: C, 59.99, H, 7.67, N, 11.73.

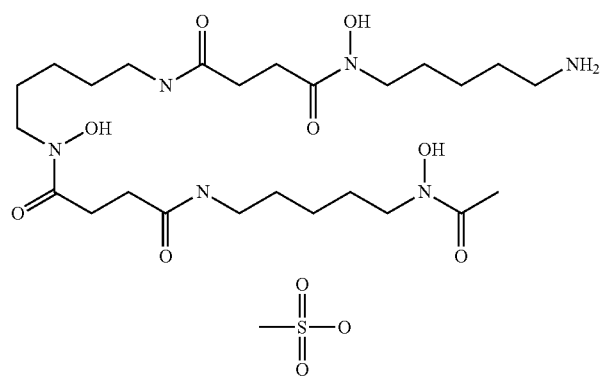

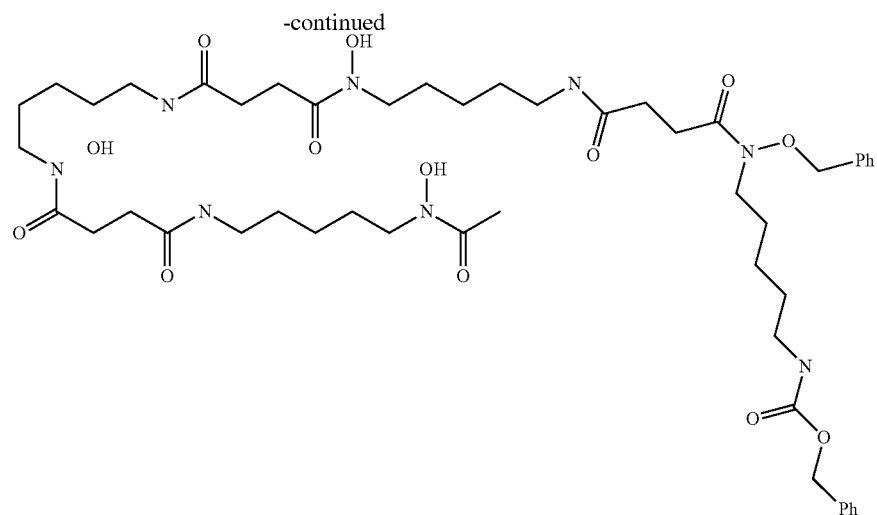

c. Synthesis of Ligand I

A mixture of compound b (125 mg, 0.13 mmol) and 100 mL of MeOH was sonicated for 10 min in an ultrasonic bath. To the resulting suspension, 10% Pd/C (38 mg) was added and hydrogenation was carried out for 6 h under $H_2$ (1 bar) atmosphere. The reaction mixture was then filtered by cotton plug followed by a filter paper. The solution was evaporated to give a white solid that was washed with 10 mL of acetonitrile and 20 mL of $Et_2O$ and dried.

Data: 1H NMR (500 MHz, DMSO-d6): δ (ppm) 1.19-1.28 (m, 8H), 1.33-1.39 (m, 7H), 1.46-1.53 (m, 9H), 1.97 (s, 3H), 2.24-2.33 (m, 8H), 2.55-2.60 (m, 6H), 2.73-2.76 (m, 2H), 2.97-3.03 (m, 6H), 3.41-3.49 (m, 8H), 7.77 (s, br, 4H), 9.60 (s, br, 3H). 13C{1H} NMR (125 MHz, DMSO-d6): δ (ppm) 20.8, 23.3, 23.9, 26.2, 26.5, 27.1, 27.9, 28.1, 29.2, 30.2, 30.3, 38.9, 39.2, 47.2, 47.5, 170.6, 171.7, 172.4, 172.5. ESI-MS (positive detection mode): m/z (%) 761.5 (100) [M+H]+. Anal. Calcd for $C_{34}H_{64}N_8O_{11}$: C, 53.67, H, 8.48, N, 14.73. Found: C, 53.60, H, 8.25, N, 14.66.

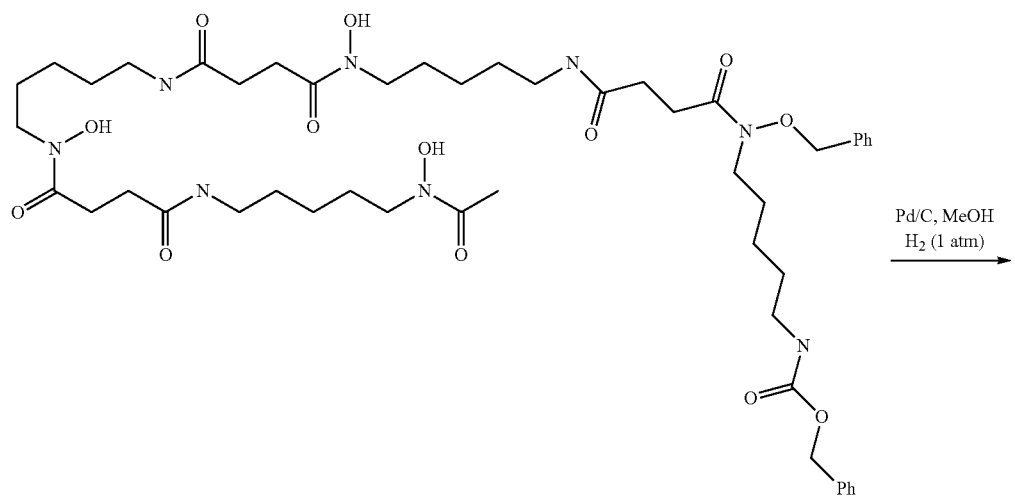

Ligand I

-continued

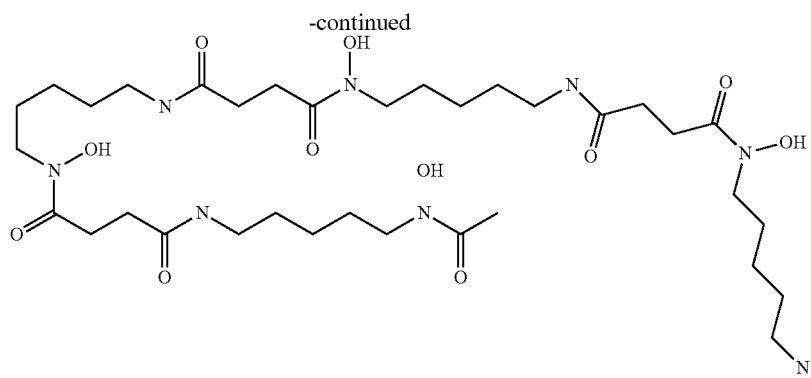

d. Synthesis of Complex I 600 uL (0.0072 mM) of a solution of the ligand I in 0.1 M HCl was added to 200 uL of the solution of $ZrCl_4$ in 0.1 M HCl. The pH of the mixture was then slowly adjusted to ca. 8 by slow addition of 0.1 M $K_2CO_3$ solution and stirred for addition 40 min. Then the mixture was lyophilized to give white solid. Formation of the desired product was confirmed by the single peak observed in the LC-MS analysis that has the expected mass.

For scaling up, to a suspension of the ligand (21.8 mg) in 667 uL of 0.1 mM HCl, a solution (667 uL, 10 mg/mL) of $ZrCl_4$ in 0.1M HCl was added and stirred for 10 min. The suspension slowly disappears during this time. The pH of the mixture was then slowly adjusted to ca. 8 by slow addition of 0.1 M $K_2CO_3$ solution, stirred for additional 1.5 h and then lyophilized to give a white solid powder.

Data: $t_R$ (LC-MS) 9.3 min. Mass 847.3 [M+H]+.

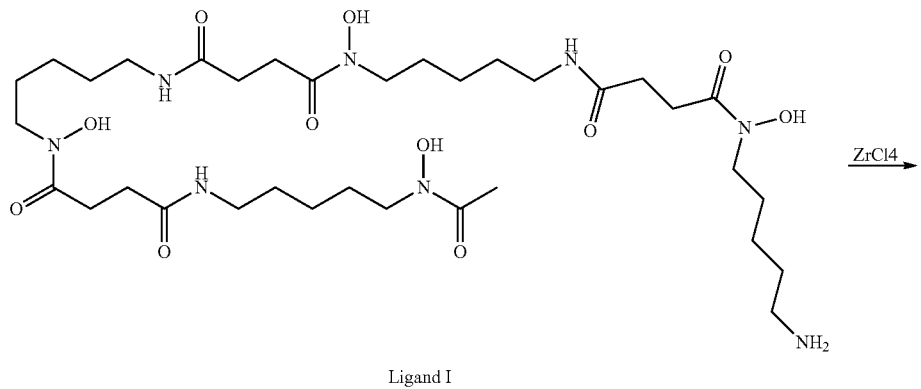

Ligand I

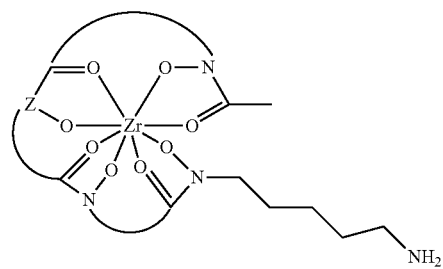

Complex I e. Synthesis of Ligand II

To a stirred mixture of ligand I (20 mg, 0.03 mmol) and succinic anhydride (3.9 mg, 0.04 mmol) in 2 mL DMF, NEt$_3$ (7.6 mg, 0.07 mmol) was added under N$_2$ atmosphere. After 48 h, DMF was removed in vacuum and the white solid obtained was washed with small portions acetone and Et$_2$O.

Data: 1H NMR (500 MHz, DMSO-d6): δ (ppm) 1.18-1.26 (m, 8H), 1.34-1.42 (m, 8H), 1.46-1.54 (m, 8H), 1.97 (s, 3H), 2.24-2.33 (m, 8H), 2.39-2.43 (m, 2H), 2.56-2.61 (m, 6H), 2.97-3.03 (m, 8H), 3.41-3.49 (m, 8H), 7.77 (s, br, 4H), 9.64 (s, br, 3H), 12.04 (s, br, 1H). 13C{1H} NMR (125 MHz, DMSO-d6): δ (ppm) 20.8, 23.9, 26.4, 28.1, 29.2, 29.6, 30.3, 30.4, 38.9, 47.2, 47.4, 170.6, 171.2, 171.7, 172.4, 174.3. ESI-MS (positive detection mode): m/z (%) 883.4 (100) [M+Na]+. Anal. Calcd for C$_{38}$H$_{68}$N$_8$O$_{14}$: C, 53.01, H, 7.96, N, 13.01. Found: C, 52.89, H, 7.73, N, 12.88.

1H NMR (500 MHz, DMSO-d6)

f. Synthesis of Complex II

Ligand II is not soluble either in 0.1 M HCl or in H$_2$O. The complexation was carried out in MeOH using zirconium (IV) acetylacetonate [Zr(acac)$_4$]. A mixture of ligand II (50 mg, 0.058 mmol) and Zr(acac)$_4$ (28.3 mg, 0.058 mmol) in 15 mL MeOH was heated at reflux for 15 h with continuous stirring under N$_2$ atmosphere. The solvent was then removed and the residue was then washed with Et$_2$O (20 mL) and acetone (10 mL). The compound was obtained as off white solid (48 mg, 87%). The compound is it not soluble in common organic solvents including DMSO. When trying to dissolve in 0.5% NaOD in D$_2$O, decomposition of the complex was observed. Therefore due to the limited solubility NMR spectra of the compound could not be obtained. However, the formation of the complex can be confirmed using LC-MS. Elemental analysis calculated for C$_{38}$H$_{64}$N$_8$O$_{14}$Zr.6H$_2$O.(CH$_3$)$_2$CO$_3$C, 44.19, H, 7.42, N, 10.06. Found C, 44.11, H, 7.04, N, 10.16.

Data: t$_R$ (LC-MS) 8.7 and 8.8 min. Mass 947.3 [M+H]+

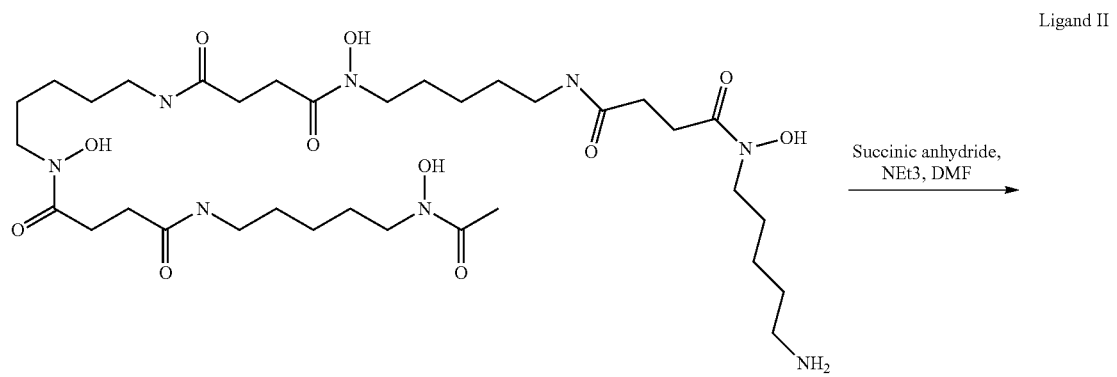

Ligand II

Succinic anhydride, NEt3, DMF

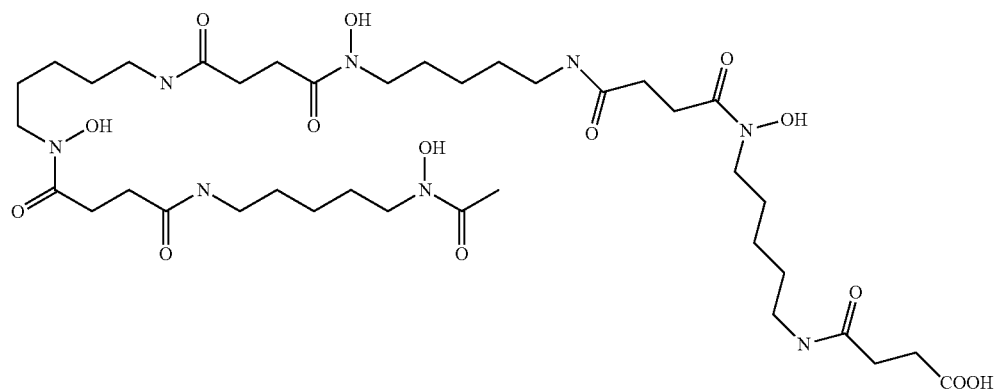

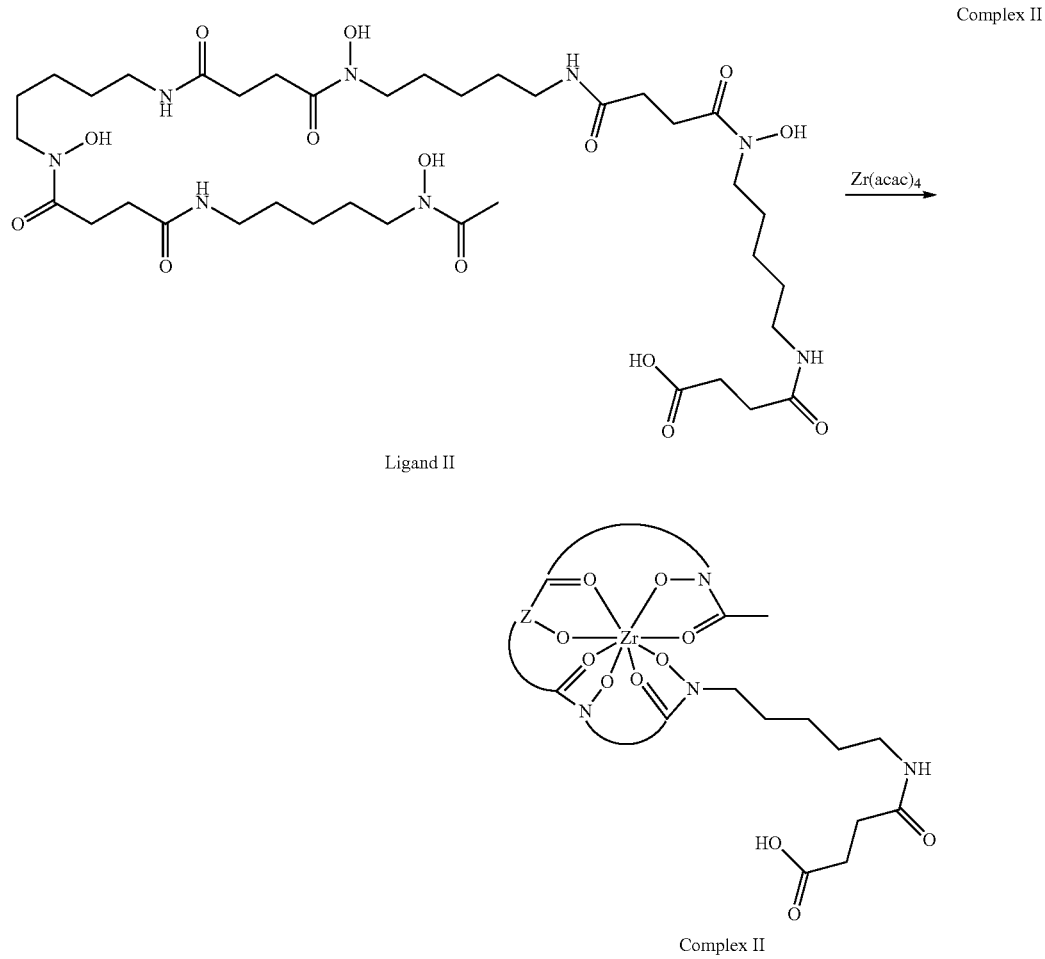

Complex II g. Synthesis of a Modified Amino Acid Sequence of Bombesin BBN$_{Ago}$(Beta-Ala)$_3$, Identical to SEQ ID NO 14: (R-Ala)$_3$-Gln-Trp-Ala-Val-Gly-Hi-Leu-14Nle-CONH$_2$ Synthesis was performed on a solid phase synthesis using an Applied Biosystem automatic peptide synthesizer with low-loaded Rink Amid resin (on a Phenomenex Jupiter 250×4.6 mm column) and standard Fmoc-protocoll, followed by HPLC analysis to test for chemical purity. Molecular Weight: 1135.32 g/mol; Chemical Formula: $C_{53}H_{82}N_{16}O_{12}$ h. Synthesis of Ligand III

Coupling of ligand II to BBN$_{Ago}$(beta-Ala)$_3$ was done by manual synthesis. 50-60 mg (9-12 µmol) of peptide resin was Fmoc-deprotected with 20% Piperidine/DMF (5×2 mL, 3-5 min each). MP-Zr-19 (2 eq.) was dissolved in 1 mL DMF (peptide grade) and shortly warmed up in a heating block at 60-70° C., then vortexed and sonicated. The solution was transferred to an eppendorff tube containing HATU (2 eq), and DIPEA (4 eq.) was added. The mixture was transferred to a syringe reactor containing the swollen peptide resin. After 3 h the reaction was stopped and the coupling procedure repeated over night. The peptide conju-

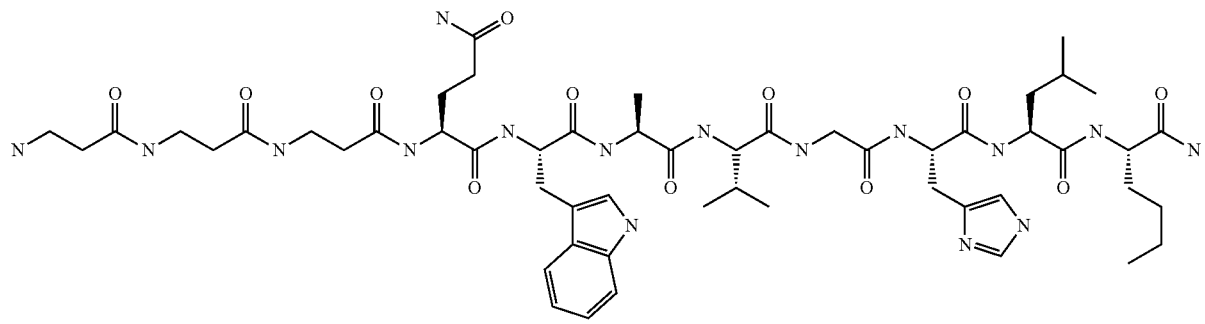

gate was cleaved from the resin with ~0.6 mL TFA/phenol/TIS/water (87.5/5/2.5/5) for 3 h and afterwards precipitated in ice cold Et$_2$O. The pellet was broken and washed three times with Et$_2$O. The remaining pellet was purified by preparative HPLC. Combined HPLC fractions were concentrated and lyophilized. ESI-MS spectra were recorded at positive electrospray ionization mode on a Bruker Esquire 3000 plus (Bruker Daltonics GmbH, Bremen, Germany) at the University of Basel. MALDI-MS analysis was performed on an Applied Biosystem 4800 TOF-TOF.

Characterization HPLC: $t_R$=9.6 min (85_60, analyt.); $t_R$=8.9 min (75_68, analyt.), $t_R$=14.8 min (75_65, prep.)

Characterization ESI-MS: m/z=990.1 [M+2H]$^{2+}$, 1979.8 [M+H]+

Characterization MALDI-MS: m/z=1978.1 [M+H]$^+$, additional signals due to degradation of chelator during measurement (e.g. 1333.7, 1533.8 break of Hydroxamate-bonds).

Molecular Weight: 1978.29 g/mol; Chemical Formula: $C_{91}H_{148}N_{24}O_{25}$

Figure 3:
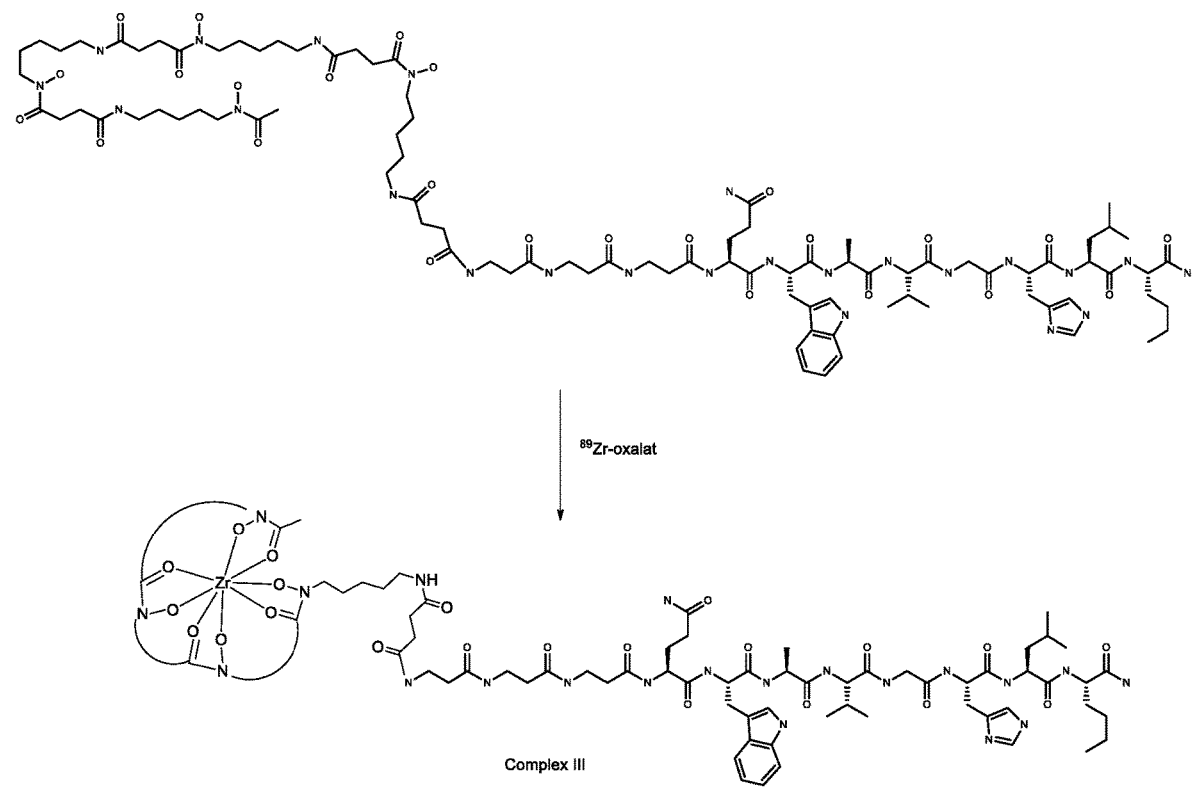
FIG. 3 shows the synthesis of complex III

Formula of ligand III and reaction: see FIG. 3

Radiolabelling and Quality Control of $^{89}$Zr-ABP-27 and $^{89}$Zr-ABP-28 i) Synthesis of Complex III

Zr-89 was obtained in 1 M oxalic acid from Perkin Elmer. ABP-27 ($M_w$=1978.29 g/mol) was prepared in lyophilized aliquots of 50 µg/50 µL and dissolved with deionized water upon starting the labeling. 10-30 µL (11.2-28.1 MBq) was taken from the Zr-89 stock solution and filled up to 200 µL with 1.0 M oxalic acid. 90 µL of 2.0 M Na$_2$CO$_3$ was added and incubated for 3 min at RT. 300 µL 0.5 M HEPES (pH 7.3), 710 µL of peptide solution (10 µg/10 µL (5 nmol)+700 µL H$_2$O) and 300 µL 0.5 M HEPES (pH 7.3) were added. The pH was checked with pH-strips and ranged from pH 7.0-7.3. The reaction solution was incubated for 240 min at ambient temperature. Quality control of radiolabelling reactions were performed by means of HPLC and ITLC. Reversed phase HPLC was done on a Bischof system equipped with HPLC pumps 2250, a λ-1010 UV-detector, a Berthold LB509 radioflow detector and a Jupiter, 4µ Proteo 90A, 250×4.6 mm column from Phenomenex. The column was eluted with mixtures of acetonitrile (solvent A) and water with 0.1% trifluoroacetic acid (TFA) (solvent B) at a flow rate of 2 mL/min and a linear gradient: 0 min 80% B, 12.5 min 60% B, 13.5 min 5% B, 14.5 min 5% B, 15 min 80% B, 17 min 80% B. 20 µL of labeling solution were diluted in 50 µL 0.1 mM Desferrioxamine in 0.5 M HEPES solution (pH 7.3) and 10 µL were injected into HPLC. Radiochemical purity was determined by manual integration and determined to be between 94-97%. ITLC was done using Biodex green ITLC-Strips. 2 µL of labelling solution were spotted directly on the strip and developed with citric acid solution (20 mM, pH 4.8) as eluent. The strip was read out with a Cyclone Plus Phosphorimager and a MultiSensitive storage phosphor screen from Perkin Elmer. Radiochemical yield was determined by manual integration and determined to be >95% j) Synthesis and Characterisation of DFO*-NCS:
Method:

DFO*(50 mg, 0.066 mmol) was dissolved in a mixture isopropanol/water (4:1, 8 mL) by means of sonication and heating. The solution was then added at room temperature drop wise to a solution of phenylenediisothiocyanate (126 mg, 0.66 mmol) in chloroform (8 mL) containing triethylamine (0.079 mmol, 0.011 mL). The reaction was stirred at room temperature. After 24 h UPLC-MS indicated complete conversion of DFO*. The solvents were concentrated under reduced pressure and the resulting white solid was washed with diethylether (4×10 mL). The product was further purified by preparative HPLC (Nucleodur Preparative column (ISIS-C18 16×250 mm 5 µm)) at a flow rate of 8 mL min$^{-1}$ with a linear gradient of A (acetonitrile (Sigma-Aldrich HPLC-grade) and B (distilled water containing 0.1% TFA): t=0 min A 36% B 64%, t=15 min A 44% B 56%, t=17 min A 36% B 64%. After lyophilisation, the product was obtained as a white powder (6 mg, 10%).

$^1$H NMR (600 MHz, DMSO-d$_6$): δ (ppm) 9.57-9.71 (m, br, 5H), 7.90 (s, br, 1H), 7.77 (s, br, 3H), 7.52-7.56 (d, 2H), 7.34-7.38 (d, 2H), 3.41-3.49 (m, 10H), 2.97-3.03 (m, 6H), 2.55-2.60 (m, 6H), 2.23-2.3 (m, 6H), 1.97 (s, 3H), 1.48-1.51 (m, 10H), 1.36-1.39 (m, 6H), 1.19-1.21 (m, 8H). $^{13}$C{$^1$H} NMR (125 MHz, DMSO-d6): δ (ppm) 180.1, 172.0, 171.3, 170.2, 139.3, 132.6, 126.2, 124.6, 123.1, 47.1, 46.8, 43.7, 38.4, 29.9, 28.8, 28.0, 27.6, 27.1, 26.0, 23.6, 23.5, 20.4. Some carbon signals were not observed due to overlapping signals. HR-ESI-MS: calcd for $C_{42}H_{68}N_{10}O_{11}S_2$/z [M+H$^+$]$^+$ 953.45887. found 953.45832, calcd for C42H68N-10O11NaS2/z [M+Na$^+$]$^+$ 975.44027. found 975.44027.

$^1$H and $^{13}$C NMR measurements were carried out on Bruker AV-600 (CP-TCl (CryoPorbe)) spectrometer and referenced to residual solvent peaks. High resolution ESI-MS spectra were recorded using a Bruker ESQUIRE-LC quadrupole ion trap instrument.

Reaction Scheme

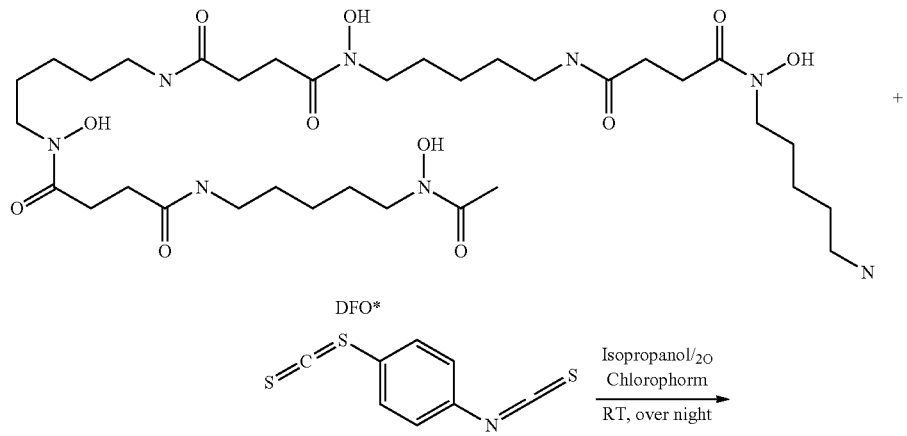

-continued

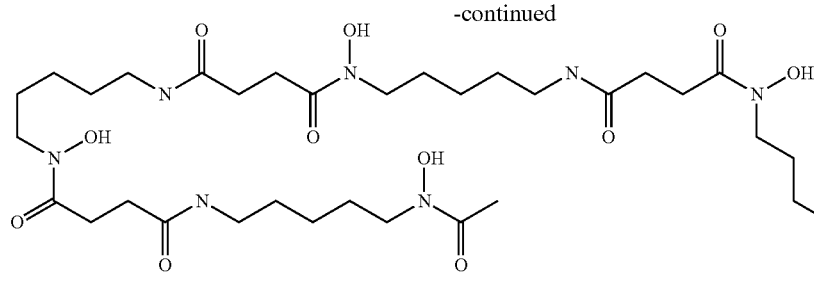

DFO*—NCS

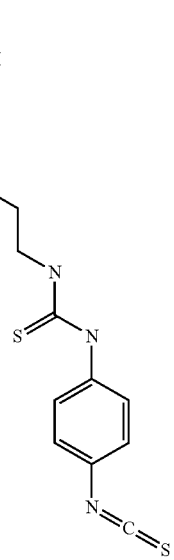

k) Synthesis of PEG Complex:

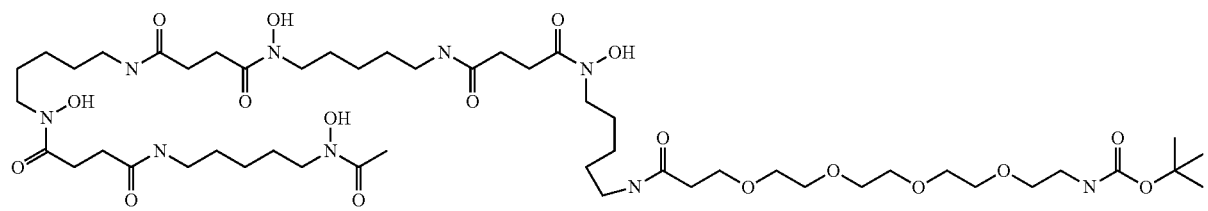 [SMILES: CC(=O)N(O)CCCCCNC(=O)CCC(=O)N(O)CCCCCNC(=O)CCC(=O)N(O)CCCCCNC(=O)CCC(=O)N(O)CCCCCNC(=O)CCOCCOCCOCCOCCNC(=O)OC(C)(C)C]

R1=Methyl
D=Hydroxymate
X=[CH$_2$]$_5$—N—[C=O]—[CH$_2$]$_2$

---

The invention claimed is:

1. A ligand having the structure

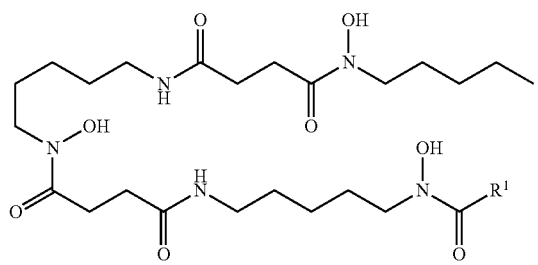

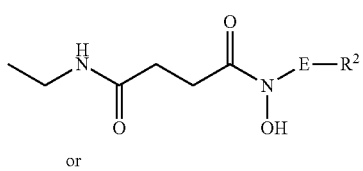

or

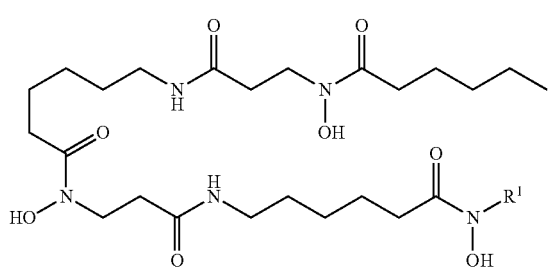

-continued

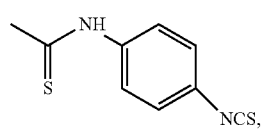

wherein $R^1$ is a $C_1$-$C_5$ alkyl, or a $C_3$-$C_6$ cycloalkyl, an arene, and/or a heteroarene, wherein the arene or heteroarene consists of between five and fifteen carbon or hetero atoms, E is a liner linker and, $R^2$ is a) an OH, $NH_2$, SH, COOH, CHO, $N_3$, SCN, $CH_2X$ with X being Cl, Br or I, an activated ester, an ene-one system, a diene/dienophile, an alkene, an alkyne, (CO)—$(CH_2)_2$—COOH, or b) a polypeptide, that specifically binds to a target site on cells and/or tissues with an association constant of lower than (<) $10^{-6}$ mol/l, $<10^{-7}$ mol/l, $<10^{-8}$ mol/l or $<10^{-9}$ mol/l, wherein the ligand binds to a metal atom selected from the group consisting of Zr, Ga, Lu and Y.

2. The ligand according to claim 1, wherein $R^1$ is methyl, ethyl or propyl and E is $(CH_2)_5$—NH—.

3. The ligand according to claim 1, described by the formula

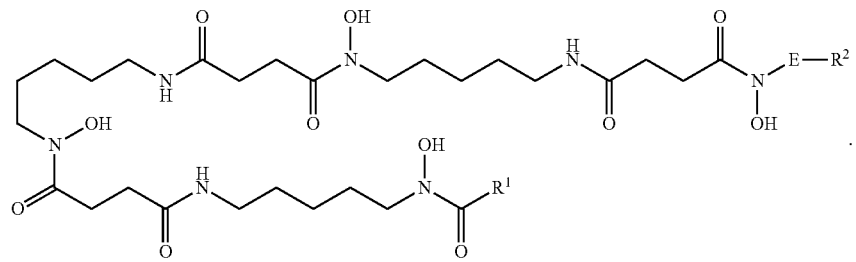

4. The ligand according to claim 1, wherein $R^2$ comprises a polypeptide being a functional homologue of bombesin, somatostatin, gastrin, trans-activator of transcription peptide, prostate-specific antigen, neuropeptide Y, octreotide, gastric inhibitory polypeptide, neurokinin A, neurotensin, exendin-3, exendin-4, or substance P, said peptide comprising an amino acid sequence of at least 80%, 85%, 90%, 95%, 98%, or 99% identity to SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, or SEQ ID NO 13, respectively.

5. A complex comprising a ligand according to claim 1, coordinatively bound to Zr, Ga, Lu or Y.

6. The ligand of claim 1, wherein the metal is Zr.

7. A complex comprising a ligand according to claim 1, wherein the metal is selected from the group consisting of $^{67}Ga$, $^{68}Ga$, $^{89}Zr$, $^{90}Y$, and $^{177}Lu$.

8. A method of synthesis of a complex comprising a ligand according to claim 1, coordinatively bound to Zr, Ga, Lu or Y comprising steps of:
(a) providing the ligand; and
(b) adding a metal selected from the group consisting of Zr, Ga, Lu and Y.

9. A method of treatment of neoplastic disease comprising administering the complex according to claim 5 to a patient in need thereof.

10. A solid support comprising the ligand of claim 1 covalently attached to a solid support.

11. The solid support according to claim 10, wherein said solid support is a nanoparticle.

12. The solid support according to claim 11, wherein said nanoparticle is selected from gold, silica, lipids, polymeric, metal or metal oxide compositions comprising the metals iron, manganese, or titanium.

13. The ligand according to claim 1, wherein $R^1$ is a methyl.

14. The ligand according to claim 1, wherein $R^2NH_2$, (CO)—$(CH_2)_2$—COOH, or $BBN_{Ago}$(Beta-Ala)$_3$.

15. The ligand according to claim 1, wherein E is $(CH_2)_5$, $(CH_2)_5NH$, or $(CH_2)_5NH$—(CO)—$(CH_2)_2$—(CO)N—.

16. The ligand according to claim 1, wherein the polypeptide is an antibody.

17. The ligand of claim 16, wherein in the antibody is trastuzumab or pertuzumab.

18. A complex comprising a ligand according to claim 1, wherein the metal is $^{89}Zr$.

19. The ligand according to claim 1, wherein $R^2$ is

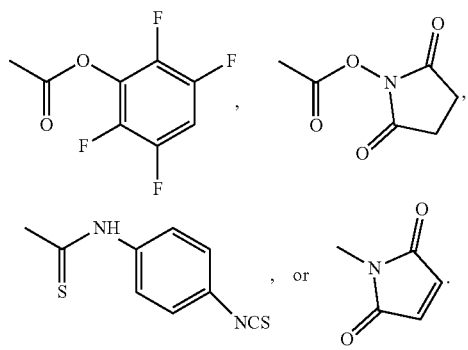

20. A solid support comprising a complex of claim 5 covalently attached to a solid support.

* * * * *